US012577282B2

(12) United States Patent
Hudalla et al.

(10) Patent No.: US 12,577,282 B2
(45) Date of Patent: Mar. 17, 2026

(54) GALECTIN-1/ GALECTIN-3 CHIMERAS AND MULTIVALENT PROTEINS

(71) Applicant: University of Florida Research Foundation, Incorporated, Gainesville, FL (US)

(72) Inventors: Gregory Allan Hudalla, Gainesville, FL (US); Margaret Mary Fettis, Northborough, MA (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1107 days.

(21) Appl. No.: 17/434,616

(22) PCT Filed: Feb. 28, 2020

(86) PCT No.: PCT/US2020/020532
§ 371 (c)(1),
(2) Date: Aug. 27, 2021

(87) PCT Pub. No.: WO2020/176900
PCT Pub. Date: Sep. 3, 2020

(65) Prior Publication Data
US 2022/0098258 A1       Mar. 31, 2022

Related U.S. Application Data

(60) Provisional application No. 62/811,771, filed on Feb. 28, 2019.

(51) Int. Cl.
*A61K 38/00*       (2006.01)
*A61P 29/00*       (2006.01)
*C07K 14/47*       (2006.01)

(52) U.S. Cl.
CPC .......... *C07K 14/4726* (2013.01); *A61P 29/00* (2018.01); *A61K 38/00* (2013.01); *C07K 2319/73* (2013.01)

(58) Field of Classification Search
CPC .............. A61K 38/00; A61P 1/04; A61P 1/16; A61P 29/00; A61P 35/00; A61P 37/06; A61P 43/00; C07K 14/4726; C07K 2319/73
See application file for complete search history.

(56) References Cited

U.S. PATENT DOCUMENTS

| | | | |
|---|---|---|---|
| 11,407,797 B2 | 8/2022 | Hudalla et al. | |
| 11,603,394 B2 | 3/2023 | Hudalla et al. | |
| 2005/0074865 A1 | 4/2005 | Afeyan et al. | |
| 2005/0220792 A1 | 10/2005 | Agou et al. | |
| 2005/0260222 A1 | 11/2005 | Gupta et al. | |
| 2007/0098701 A1 | 5/2007 | Okano et al. | |
| 2008/0234177 A1 * | 9/2008 | Bremer .................. | A61P 29/00 530/370 |
| 2011/0294983 A1 | 12/2011 | Desmet et al. | |
| 2011/0318372 A1 | 12/2011 | Andersen et al. | |
| 2014/0187487 A1 | 7/2014 | Choichet et al. | |
| 2017/0335311 A1 | 11/2017 | Gruskin et al. | |
| 2018/0073007 A9 | 3/2018 | Gruskin et al. | |
| 2019/0218264 A1 | 7/2019 | Hudalla et al. | |
| 2020/0262882 A1 | 8/2020 | Hudalla et al. | |
| 2022/0106580 A1 | 4/2022 | Hudalla et al. | |

FOREIGN PATENT DOCUMENTS

| | | |
|---|---|---|
| EP | 1748050 | 1/2007 |
| JP | 2005-537032 A | 12/2005 |
| JP | 2009-515520 A | 4/2009 |
| JP | 2011-520783 A | 7/2011 |
| JP | 2012-514616 A | 6/2012 |
| JP | 2015-528514 A | 9/2015 |
| JP | 2016-040260 A | 3/2016 |
| WO | WO 1999/012041 A1 | 3/1999 |
| WO | WO 2003/090780 A1 | 11/2003 |
| WO | WO 2004/019878 A2 | 3/2004 |
| WO | WO 2007/058776 A2 | 5/2007 |
| WO | WO 2009/143843 A1 | 12/2009 |
| WO | WO 2010/078966 A1 | 7/2010 |
| WO | WO 2011/034605 A2 | 3/2011 |
| WO | WO 2014/043708 A1 | 3/2014 |
| WO | WO 2014/089267 A1 | 6/2014 |
| WO | WO 2016/127100 A1 | 8/2016 |
| WO | WO-2016172319 A1 * | 10/2016 ............. A61K 38/16 |
| WO | WO-2018067660 A1 * | 4/2018 ................ A61P 1/02 |

OTHER PUBLICATIONS

Vinson et al. (Mol Cell Biol. Sep. 2002; 22(18): 6321-6335). Classification of Human B-ZIP Proteins Based on Dimerization Properties. (Year: 2002).*

Dang et al. Front Chem. Feb. 8, 2022;10:829312. Molecular Approaches to Protein Dimerization: Opportunities for Supramolecular Chemistry (Year: 2022).*

Friedberg, Automated protein function prediction—the genomic challenge. Brief Bioinform. Sep. 2006;7(3):225-42. doi: 10.1093/bib/bb1004. Epub May 23, 2006.

Lee et al., Heme-binding-mediated negative regulation of the tryptophan metabolic enzyme indoleamine 2,3-dioxygenase 1 (IDO1) by IDO2. Exp Mol Med. Nov. 14, 2014;46(11):e121. doi: 10.1038/emm.2014.69.

Thornton et al., From structure to function: approaches and limitations. Nat Struct Biol. Nov. 2000;7 Suppl:991-4. doi: 10.1038/80784.

International Search Report and Written Opinion mailed Jan. 4, 2019 for Application No. PCT/US2018/055213.

International Preliminary Report on Patentability mailed Apr. 23, 2020 for Application No. PCT/US2018/055213.

(Continued)

*Primary Examiner* — Lianko G Garyu
*Assistant Examiner* — Mercy H Sabila
(74) *Attorney, Agent, or Firm* — Wolf, Greenfield & Sacks, P.C.

(57) ABSTRACT

Described herein are Galectin-1/Galectin-3 multivalent protein complexes and uses thereof. In some aspects, Galectin-1/Galectin-3 multivalent protein complexes are useful to treat inflammatory conditions in a subject.

19 Claims, 12 Drawing Sheets
Specification includes a Sequence Listing.

(56)         References Cited

OTHER PUBLICATIONS

Extended European Search Report for Application No. EP 17859087. 3, mailed Apr. 8, 2020.

International Search Report and Written Opinion for Application No. PCT/US2017/055076, mailed Feb. 21, 2018.

International Preliminary Report on Patentability for Application No. PCT/US2017/055076, mailed Apr. 18, 2019.

Invitation to Pay Additional Fees for Application No. PCT/US2020/020532, mailed May 21, 2020.

International Search Report and Written Opinion for Application No. PCT/US2020/020532, mailed Jul. 24, 2020.

International Preliminary Report on Patentability for Application No. PCT/US2020/020532, mailed Sep. 10, 2021.

International Search Report and Written Opinion for Application No. PCT/US2019/058230, mailed Feb. 5, 2020.

International Preliminary Report on Patentability for Application No. PCT/US2019/058230, mailed May 6, 2021.

[No Author Listed], Plasmid Files. SnapGene. Retrieved from www.snapgene.com/resources/plasmid-files/?set=pgex_vectors_(ge_healthcare)&plasmid=pGEX-4T-1. Accessed on Nov. 4, 2021. 5 pages.

Brooks et al., Immunomodulatory Factors Galectin-9 and Interferon-Gamma Synergize to Induce Expression of Rate-Limiting Enzymes of the Kynurenine Pathway in the Mouse Hippocampus. Front Immunol. Oct. 17, 2016;7:422. doi: 10.3389/fimmu.2016.00422.

Fettis et al., Engineering Reactive Oxygen Species-Resistant Galectin-1 Dimers with Enhanced Lectin Activity. Bioconjug Chem. Jul. 18, 2018;29(7):2489-2496. doi: 10.1021/acs.bioconjchem.8b00425. Epub Jul. 3, 2018.

Iken et al., Indoleamine 2,3-dioxygenase and metabolites protect murine lung allografts and impair the calcium mobilization of T cells. Am J Respir Cell Mol Biol. Oct. 2012;47(4):405-16. doi: 10.1165/rcmb.2011-0438OC. Epub Apr. 19, 2012.

Inohara et al., Cytoplasmic and serum galectin-3 in diagnosis of thyroid malignancies. Biochem Biophys Res Commun. Nov. 21, 2008;376(3):605-10. doi: 10.1016/j.bbrc.2008.09.041. Epub Sep. 20, 2008.

Krylov et al., Leucine Zipper. Encyclopedia of Life Sciences. 2001. 7 pages.

Li et al., Rate enhancement of an interfacial biochemical reaction through localization of substrate and enzyme by an adaptor domain. J Phys Chem B. Nov. 25, 2010;114(46):15113-8. doi: 10.1021/jp102820e. Epub Nov. 3, 2010.

Litowski et al., Designing heterdimeric two-stranded alpha-helical coiled-coils. J Biol Chem. Oct. 4, 2002;277(40):37272-9.

Littlejohn et al., Expression and purification of recombinant human indoleamine 2, 3-dioxygenase. Protein Expr Purif. Jun. 2000;19(1):22-9. doi: 10.1006/prep.2000.1214.

Liu et al., Expression of immune checkpoint molecules in endometrial carcinoma. Exp. Ther Med. 2015;10(5):1947-52.

Liu et al., Galectins as molulators of tumor progression. Nat. Rev. Cancer. 2005;5(1):29-41.

Nishi et al., Functional and structural bases of a cysteine-less mutant as a long-lasting substitute for galectin-1. Glycobiology. Dec. 2008;18(12):1065-73. doi: 10.1093/glycob/cwn089. Epub Sep. 16, 2008.

Pechar et al., Coiled coil peptides and polymer-peptide conjugates: synthesis, self-assembly, characterization and potential in drug delivery systems. Biomacromolecules. Jul. 14, 2014;15(7):2590-9. doi: 10.1021/bm500436p. Epub Jun. 3, 2014.

Weidle, et al. Fully Human Targeted Cytotoxic Fusion Proteins: New Anticancer Agents on the Horizon. Cancer Genomics Proteomics. 2012;9:119-33.

Weisel et al., Fibrin Formation, Structure and Properties. Subcell Biochem. 2017;82:405-456. doi: 10.1007/978-3-319-49674-0_13. Author Manuscript, 52 pages.

Wheeldon et al., Substrate channeling as an approach to cascade reactions. Nat Chem. Apr. 8, 2016:4;299-309.

Chen et al., Expression, purification and thermostability of MBP-chondroitinase ABC I from Proteus vulgaris. Int J Biol Macromol. Jan. 2015;72:6-10. doi: 10.1016/j.ijbiomac.2014.07.040. Epub Jul. 29, 2014.

Pakulska et al., Affinity-based release of chondroitinase ABC from a modified methylcellulose hydrogel. J Control Release. Oct. 10, 2013;171(1):11-6. doi: 10.1016/j.jconrel.2013.06.029. Epub Jul. 2, 2013.

* cited by examiner

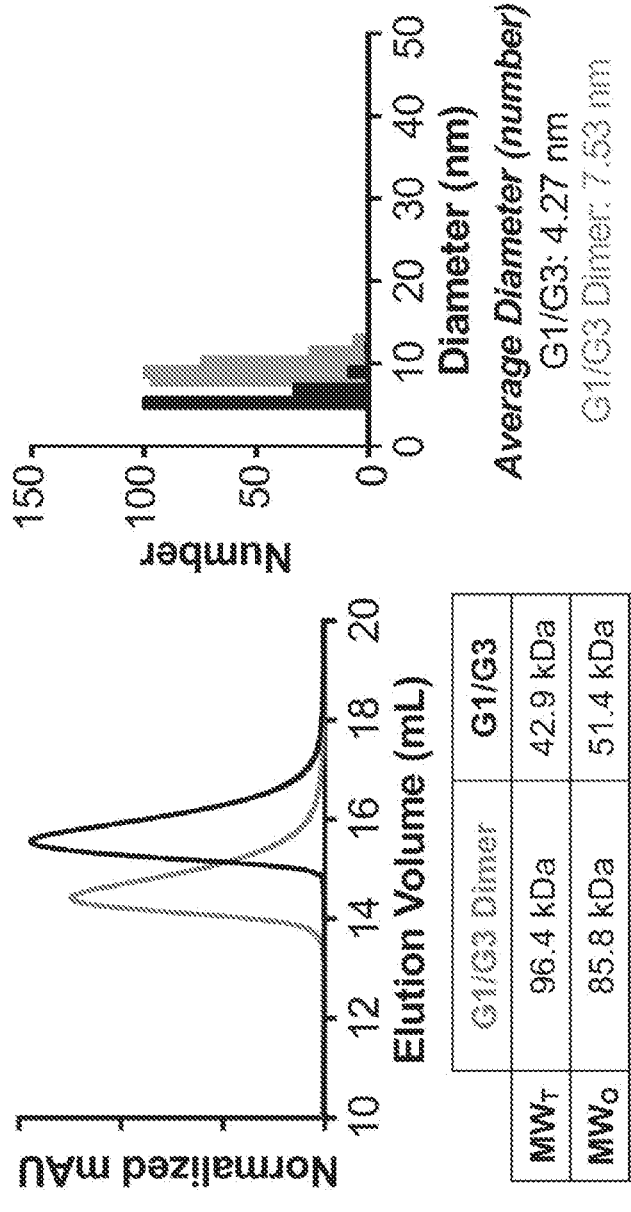
FIG. 2C
FIG. 2B
| | G1/G3 Dimer | G1/G3 |
|---|---|---|
| MW$_T$ | 96.4 kDa | 42.9 kDa |
| MW$_O$ | 85.8 kDa | 51.4 kDa |
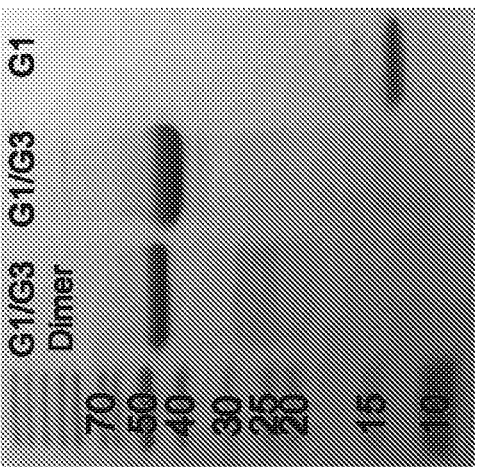
Denatured MW$_T$
G1/G3 Dimer: 48.2 kDa
G1/G3: 42.9 kDa
G1: 14.7 kDa
FIG. 2A 5μM Protein - 18 Hours 0.5μM Protein - 18 Hours 5µM Protein - 4 Hours

| G1 | G1 - PEG-G1 | G1/G3 | G1/G3 Dimer |

0.5µM Protein - 4 Hours

| G1 | G1 - PEG-G1 | G1/G3 | G1/G3 Dimer |

Serum Free Media, 5 µM Protein - 18 Hours

| G1 | G1 - PEG-G1 | G1/G3 Dimer |

Serum Free Media, 0.5 µM Protein - 18 Hours

| G1 | G1 - PEG-G1 | G1/G3 Dimer |

G1 - PEG-G1

PEGylation of G1/G3

SEQUENCE LISTING

<160> NUMBER OF SEQ ID NOS: 11

<210> SEQ ID NO 1
<211> LENGTH: 135
<212> TYPE: PRT
<213> ORGANISM: Homo sapiens

<400> SEQUENCE: 1

Met Ala Ser Gly Leu Val Ala Ser Asn Leu Asn Leu Lys Pro Gly Glu
1               5                   10                 15

Ser Leu Arg Val Arg Gly Glu Val Ala Pro Asp Ala Lys Ser Phe Val
          20                   25                   30

```
Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Val Asp Gly Asp Phe Lys
        115                 120                 125

Ile Lys Ser Val Ala Phe Asp
        130                 135

<210> SEQ ID NO 2
<211> LENGTH: 408
<212> TYPE: PRT
<213> ORGANISM: Homo sapiens
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (402)..(408)
<223> OTHER INFORMATION: may or may not be present

<400> SEQUENCE: 2

Met Ala Ser Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Ser Val Ala Phe Asp Gly Ser Gly Gly Ser Gly Gly Ser
        130                 135                 140

Gly Gly Ser Gly Gly Glu Phe Ala Asp Asn Phe Ser Leu His Asp Ala
145                 150                 155                 160

Leu Ser Gly Ser Gly Asn Pro Asn Xaa Gln Gly Trp Pro Gly Ala Trp
                165                 170                 175

Gly Asn Gln Pro Ala Gly Ala Gly Gly Tyr Pro Gly Ala Ser Tyr Pro
                180                 185                 190

Gly Ala Tyr Pro Gly Gln Ala Pro Pro Gly Ala Tyr Pro Gly Gln Ala
            195                 200                 205

Pro Pro Gly Ala Tyr Pro Gly Ala Pro Gly Ala Tyr Pro Gly Ala Pro
        210                 215                 220
```

-continued

```
Ala Pro Gly Val Tyr Pro Gly Pro Pro Ser Gly Pro Gly Ala Tyr Pro
225             230             235             240

Ser Ser Gly Gln Pro Ser Ala Pro Gly Ala Tyr Pro Ala Thr Gly Pro
            245             250             255

Tyr Gly Ala Pro Ala Gly Pro Leu Ile Val Pro Tyr Asn Leu Pro Leu
            260             265             270

Pro Gly Gly Val Val Pro Arg Met Leu Ile Thr Ile Leu Gly Thr Val
            275             280             285

Lys Pro Asn Ala Asn Arg Ile Ala Leu Asp Phe Gln Arg Gly Asn Asp
    290             295             300

Val Ala Phe His Phe Asn Pro Arg Phe Asn Glu Asn Asn Arg Arg Val
305             310             315             320

Ile Val Cys Asn Thr Lys Leu Asp Asn Asn Trp Gly Arg Glu Glu Arg
            325             330             335

Gln Ser Val Phe Pro Phe Glu Ser Gly Lys Pro Phe Lys Ile Gln Val
            340             345             350

Leu Val Glu Pro Asp His Phe Lys Val Ala Val Asn Asp Ala His Leu
    355             360             365

Leu Gln Tyr Asn His Arg Val Lys Lys Leu Asn Glu Ile Ser Lys Leu
    370             375             380

Gly Ile Ser Gly Asp Ile Asp Leu Thr Ser Ala Ser Tyr Asn Met Ile
385             390             395             400

Leu Glu His His His His His His
            405
```

```
<210> SEQ ID NO 3
<211> LENGTH: 460
<212> TYPE: PRT
<213> ORGANISM: Homo sapiens
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (454)..(460)
<223> OTHER INFORMATION: may or may not be present

<400> SEQUENCE: 3
```

```
Met Ala Ser Gly Leu Val Ala Ser Asn Leu Asn Leu Lys Pro Gly Glu
1               5               10              15

Ser Leu Arg Val Arg Gly Glu Val Ala Pro Asp Ala Lys Ser Phe Val
            20              25              30

Leu Asn Leu Gly Lys Asp Ser Asn Asn Leu Cys Leu His Phe Asn Pro
            35              40              45

Arg Phe Asn Ala His Gly Asp Ala Asn Thr Ile Val Cys Asn Ser Lys
    50              55              60

Asp Gly Gly Ala Trp Gly Thr Glu Gln Arg Glu Ala Val Phe Pro Phe
65              70              75              80

Gln Pro Gly Ser Val Ala Glu Val Ser Ile Thr Phe Asp Gln Ala Asn
            85              90              95

Leu Thr Val Lys Leu Pro Asp Gly Tyr Glu Phe Lys Phe Pro Asn Arg
            100             105             110

Leu Asn Leu Glu Ala Ile Asn Tyr Met Ala Ala Asp Gly Asp Phe Lys
    115             120             125

Ile Lys Ser Val Ala Phe Asp Gly Ser Gly Gly Ser Gly Gly Ser
    130             135             140
```

-continued

```
Gly Gly Ser Gly Gly Met Ala Arg Met Lys Gln Leu Glu Asp Lys Val
145             150                 155                 160

Glu Glu Leu Leu Ser Lys Asn Tyr His Leu Glu Asn Glu Val Ala Arg
                165                 170                 175

Leu Lys Lys Leu Val Gly Glu Arg Gly Gly Gly Ser Gly Gly Ser Gly
            180                 185                 190

Gly Gly Gly Ser Gly Gly Ser Gly Gly Glu Phe Ala Asp Asn Phe Ser
            195                 200                 205

Leu His Asp Ala Leu Ser Gly Ser Gly Asn Pro Asn Xaa Gln Gly Trp
    210                 215                 220

Pro Gly Ala Trp Gly Asn Gln Pro Ala Gly Ala Gly Gly Tyr Pro Gly
225                 230                 235                 240

Ala Ser Tyr Pro Gly Ala Tyr Pro Gly Gln Ala Pro Pro Gly Ala Tyr
                245                 250                 255

Pro Gly Gln Ala Pro Pro Gly Ala Tyr Pro Gly Ala Pro Gly Ala Tyr
                260                 265                 270

Pro Gly Ala Pro Ala Pro Gly Val Tyr Pro Gly Pro Pro Ser Gly Pro
            275                 280                 285

Gly Ala Tyr Pro Ser Ser Gly Gln Pro Ser Ala Pro Gly Ala Tyr Pro
    290                 295                 300

Ala Thr Gly Pro Tyr Gly Ala Pro Ala Gly Pro Leu Ile Val Pro Tyr
305                 310                 315                 320

Asn Leu Pro Leu Pro Gly Gly Val Val Pro Arg Met Leu Ile Thr Ile
                325                 330                 335

Leu Gly Thr Val Lys Pro Asn Ala Asn Arg Ile Ala Leu Asp Phe Gln
            340                 345                 350

Arg Gly Asn Asp Val Ala Phe His Phe Asn Pro Arg Phe Asn Glu Asn
        355                 360                 365

Asn Arg Arg Val Ile Val Cys Asn Thr Lys Leu Asp Asn Asn Trp Gly
    370                 375                 380

Arg Glu Glu Arg Gln Ser Val Phe Pro Phe Glu Ser Gly Lys Pro Phe
385                 390                 395                 400

Lys Ile Gln Val Leu Val Glu Pro Asp His Phe Lys Val Ala Val Asn
                405                 410                 415

Asp Ala His Leu Leu Gln Tyr Asn His Arg Val Lys Lys Leu Asn Glu
            420                 425                 430

Ile Ser Lys Leu Gly Ile Ser Gly Asp Ile Asp Leu Thr Ser Ala Ser
        435                 440                 445

Tyr Asn Met Ile Leu Glu His His His His His
    450                 455                 460

<210> SEQ ID NO 4
<211> LENGTH: 259
<212> TYPE: PRT
<213> ORGANISM: Homo sapiens

<400> SEQUENCE: 4

Glu Phe Ala Asp Asn Phe Ser Leu His Asp Ala Leu Ser Gly Ser Gly
1               5                   10                  15

Asn Pro Asn Pro Gln Gly Trp Pro Gly Ala Trp Gly Asn Gln Pro Ala
            20                  25                  30

Gly Ala Gly Gly Tyr Pro Gly Ala Ser Tyr Pro Gly Ala Tyr Pro Gly
        35                  40                  45

Gln Ala Pro Pro Gly Ala Tyr Pro Gly Gln Ala Pro Pro Gly Ala Tyr
    50                  55                  60
```

```
Pro Gly Ala Pro Gly Ala Tyr Pro Gly Ala Pro Ala Pro Gly Val Tyr
65              70                  75                  80

Pro Gly Pro Pro Ser Gly Pro Gly Ala Tyr Pro Ser Ser Gly Gln Pro
                85                  90                  95

Ser Ala Pro Gly Ala Tyr Pro Ala Thr Gly Pro Tyr Gly Ala Pro Ala
            100                 105                 110

Gly Pro Leu Ile Val Pro Tyr Asn Leu Pro Leu Pro Gly Gly Val Val
        115                 120                 125

Pro Arg Met Leu Ile Thr Ile Leu Gly Thr Val Lys Pro Asn Ala Asn
    130                 135                 140

Arg Ile Ala Leu Asp Phe Gln Arg Gly Asn Asp Val Ala Phe His Phe
145                 150                 155                 160

Asn Pro Arg Phe Asn Glu Asn Asn Arg Arg Val Ile Val Cys Asn Thr
                165                 170                 175

Lys Leu Asp Asn Asn Trp Gly Arg Glu Glu Arg Gln Ser Val Phe Pro
            180                 185                 190

Phe Glu Ser Gly Lys Pro Phe Lys Ile Gln Val Leu Val Glu Pro Asp
            195                 200                 205

His Phe Lys Val Ala Val Asn Asp Ala His Leu Leu Gln Tyr Asn His
    210                 215                 220

Arg Val Lys Lys Leu Asn Glu Ile Ser Lys Leu Gly Ile Ser Gly Asp
225                 230                 235                 240

Ile Asp Leu Thr Ser Ala Ser Tyr Asn Met Ile Leu Glu His His His
                245                 250                 255

His His His
```

```
<210> SEQ ID NO 5
<211> LENGTH: 66
<212> TYPE: PRT
<213> ORGANISM: Homo sapiens
<220> FEATURE:
<221> NAME/KEY: misc_feature
<222> LOCATION: (15)..(49)
<223> OTHER INFORMATION: is a dimerization sequence

<400> SEQUENCE: 5
```

```
Gly Ser Gly Gly Gly Ser Gly Gly Ser Gly Gly Ser Gly Gly Met Ala
1               5                   10                  15

Arg Met Lys Gln Leu Glu Asp Lys Val Glu Glu Leu Leu Ser Lys Asn
                20                  25                  30

Tyr His Leu Glu Asn Glu Val Ala Arg Leu Lys Lys Leu Val Gly Glu
            35                  40                  45

Arg Gly Gly Gly Ser Gly Gly Ser Gly Gly Gly Gly Ser Gly Gly Ser
    50                  55                  60

Gly Gly
65
```

```
<210> SEQ ID NO 6
<211> LENGTH: 1359
<212> TYPE: DNA
<213> ORGANISM: Homo sapiens

<400> SEQUENCE: 6
```

```
atggctagtg gtctggtcgc cagcaacctg aatctcaaac ctggagagag ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
```

-continued

```
tgcaacagca aggacggcgg ggcctggggg accgagcagc gggaggctgt ctttcccttc      240
cagcctggaa gtgttgcaga ggtgagcatc accttcgacc aggccaacct gaccgtcaag      300
ctgccagatg gatacgagtt caagttcccc aaccgcctca acctggaggc catcaactac      360
atggcagctg acggtgactt caagatcaaa agtgtggcct ttgacggatc cggcggcggc      420
agcggcggca gcggcggcag cggcggcatg gcgcgcatga aacagctgga agataaagtg      480
gaagaactgc tgagcaaaaa ctatcatctg gaaaacgaag tggcgcgcct gaaaaaactg      540
gtgggcgaac gcggcggcgg cagcggcggc agcggcggcg gcggcagcgg cggcagcggc      600
gaattcgcag acaattttc gctccatgat gcgttatctg ggtctggaaa cccaaaccct      660
caaggatggc ctggcgcatg ggggaaccag cctgctgggg cagggggcta cccaggggct      720
tcctatcctg gggcctaccc cgggcaggca ccccaggggg cttatcctgg acaggcacct      780
ccaggcgcct accctggagc acctggagct tatcccggag cacctgcacc tggagtctac      840
ccagggccac ccagcggccc tggggcctac ccatcttctg gacagccaag tgcccccgga      900
gcctaccctg ccactggccc ctatggcgcc cctgctgggc cactgattgt gccttataac      960 ctgccttttgc ctgggggagt ggtgcctcgc atgctgataa caattctggg cacggtgaag     1020
cccaatgcaa acagaattgc tttagatttc caaagaggga atgatgttgc cttccacttt      1080
aacccacgct tcaatgagaa caacaggaga gtcattgttt gcaatacaaa gctggataat      1140
aactggggaa gggaagaaag acagtcggtt ttcccatttg aaagtgggaa accattcaaa      1200
atacaagtac tggttgaacc tgaccacttc aaggttgcag tgaatgatgc tcacttgttg      1260
cagtacaatc atcgggttaa aaaactcaat gaaatcagca aactgggaat ttctggtgac      1320
atagacctca ccagtgcttc atataacatg atactcgag                            1359
```

<210> SEQ ID NO 7
<211> LENGTH: 405
<212> TYPE: DNA
<213> ORGANISM: Homo sapiens

<400> SEQUENCE: 7

```
atggctagtg gtctggtcgc cagcaacctg aatctcaaac ctggagagag ccttcgagtg       60
cgaggcgagg tggctcctga cgctaagagc ttcgtgctga acctgggcaa agacagcaac      120
aacctgtgcc tgcacttcaa ccctcgcttc aacgcccacg cgacgccaa caccatcgtg       180 tgcaacagca aggacggcgg ggcctggggg accgagcagc gggaggctgt ctttcccttc      240
cagcctggaa gtgttgcaga ggtgagcatc accttcgacc aggccaacct gaccgtcaag      300
ctgccagatg gatacgagtt caagttcccc aaccgcctca acctggaggc catcaactac      360
atggcagctg acggtgactt caagatcaaa agtgtggcct ttgac                      405
```

<210> SEQ ID NO 8
<211> LENGTH: 747
<212> TYPE: DNA
<213> ORGANISM: Homo sapiens

<400> SEQUENCE: 8

```
gcagacaatt tttcgctcca tgatgcgtta tctgggtctg aaacccaaa ccctcaagga       60 tggcctggcg catgggggaa ccagcctgct ggggcagggg gctacccagg ggcttcctat      120
```

-continued

```
cctggggcct accccgggca ggcacccca ggggcttatc ctggacaggc acctccaggc      180
gcctaccctg gagcacctgg agcttatccc ggagcacctg cacctggagt ctacccaggg      240
ccacccagcg gccctggggc ctacccatct tctggacagc caagtgcccc cggagcctac      300
cctgccactg gcccctatgg cgccctgct gggccactga ttgtgcctta taacctgcct        360
ttgcctgggg gagtggtgcc tcgcatgctg ataacaattc tgggcacggt gaagcccaat      420
gcaaacagaa ttgctttaga tttccaaaga gggaatgatg ttgccttcca ctttaaccca      480
cgcttcaatg agaacaacag gagagtcatt gtttgcaata caaagctgga taataactgg      540
ggaagggaag aaagacagtc ggttttccca tttgaaagtg ggaaaccatt caaaatacaa      600
gtactggttg aacctgacca cttcaaggtt gcagtgaatg atgctcactt gttgcagtac      660
aatcatcggg ttaaaaaact caatgaaatc agcaaactgg gaatttctgg tgacatagac      720
ctcaccagtg cttcatataa catgata                                          747
```

```
<210> SEQ ID NO 9
<211> LENGTH: 35
<212> TYPE: PRT
<213> ORGANISM: Homo sapiens

<400> SEQUENCE: 9

Met Ala Arg Met Lys Gln Leu Glu Asp Lys Val Glu Glu Leu Leu Ser
1               5                   10                  15

Lys Asn Tyr His Leu Glu Asn Glu Val Ala Arg Leu Lys Lys Leu Val
            20                  25                  30

Gly Glu Arg
        35

<210> SEQ ID NO 10
<211> LENGTH: 14
<212> TYPE: PRT
<213> ORGANISM: Homo sapiens

<400> SEQUENCE: 10

Gly Ser Gly Gly Gly Ser Gly Gly Ser Gly Gly Ser Gly Gly
1               5                   10

<210> SEQ ID NO 11
<211> LENGTH: 17
<212> TYPE: PRT
<213> ORGANISM: Homo sapiens

<400> SEQUENCE: 11

Gly Gly Gly Ser Gly Gly Ser Gly Gly Gly Gly Ser Gly Gly Ser Gly
1               5                   10                  15

Gly
```

GALECTIN-1/ GALECTIN-3 CHIMERAS AND MULTIVALENT PROTEINS

CROSS-REFERENCE TO RELATED APPLICATIONS

This application is a national stage filing under 35 U.S.C. 371 of International Patent Application Serial No. PCT/US2020/020532, filed Feb. 28, 2020, which claims the benefit under 35 USC 119(e) of the filing date of U.S. Patent Application Ser. No. 62/811,771, filed Feb. 28, 2019. The contents of the above-referenced applications are hereby incorporated herein in their entirety by reference.

STATEMENT REGARDING FEDERALLY SPONSORED RESEARCH

This invention was made with government support under Grant Number EB019684 awarded by the National Institutes of Health. The government has certain rights in the invention.

BACKGROUND OF THE INVENTION

Galectins, a 15-member family of soluble carbohydrate-binding proteins, are interesting as therapeutic targets for immunotherapy and immunomodulation due to their role as extracellular signals that regulate innate and adaptive immune cell phenotype and function. However, different galectins can have redundant, synergistic, and/or antagonistic signaling activity in normal immunological responses, such as resolution of inflammation and induction of antigen-specific tolerance. In addition, certain galectins can be used to promote progression of immune-pathologies, such as tumor immune privilege, metastasis, and viral infection, while others can inhibit these processes.

SUMMARY OF THE INVENTION

Although glycobiology research was first recognized in the early 19th century, researchers are just now beginning to understand the complex role of lectins and glycans within the immune system.[1,2] Galectins are a family of soluble, beta-galactoside-binding lectins that regulate the phenotype and function of various immune cells during the initiation and resolution of immune responses.[3] For example, galectin-1 (G1) and galectin-3 (G3) are mediators of tumor immunosuppression and fetal-maternal tolerance, regulate autoimmune disease progression, can enhance or inhibit viral infection, and induce pro-inflammatory responses during osteoarthritis.[4-10]

Extracellular G1 and G3 can act on innate immune cells, including monocytes, macrophages, neutrophils, and dendritic cells, yet it is their influence on T cells that receives the most attention for immunotherapy.[11-18] Extracellular G1 and G3 can induce T cell apoptosis, regulate antigen-specific T cell activation, and alter T cell cytokine secretion.[19] Despite sharing binding affinity for beta-galactoside glycans, though, G1 and G3 often evoke these changes in T cells by recognizing different cell surface glycoproteins, suggesting they function through different signalling pathways.[19,20] For example, although both G1 and G3 bind to CD45, only G1 induces CD45 clustering to trigger T cell apoptosis.[21] Both G1 and G3 have been shown to interact with CD7, yet G3 binding to CD7 does not trigger T cell death.[22-24] G1 can bind to CD2 and CD3, whereas G3 binding to these glycoproteins has not been observed.[22,24] G1 can also selectively induce death of T helper (Th)1 and Th17 cells, yet has no effect on Th2 and regulatory T cells, due to polarization-induced changes in the T cell surface glycosylation profile.[25] Similarly, G3 preferentially kills double-negative thymocytes, but not double-positive thymocytes, again due to alterations in the surface glycosylation profile of cells as they mature or polarize.[22] Interestingly, a combination of G1 and G3 did not have an additive or synergistic effect on T cell apoptosis, but rather elicited a similar extent of cell death as either galectin alone, possibly due to competitive interactions with CD45 or other T cell surface glycoproteins.[22] Beyond apoptosis, G1 has been shown to stimulate antigen-specific T cell responses while G3 antagonized these responses, yet in other contexts both G1 and G3 can regulate T cell receptor clustering and signaling.[26] Finally, G1 and G3 also have differing effects on T cell cytokine secretion, with low concentration G3 inducing IL-2 secretion, while G1 upregulates IL-10 expression by Th17 cells.[27,28]

In light of these diverse effects on T cells, exogenous galectins and engineered variants have been evaluated as therapeutics to regulate adaptive immunity in various contexts.[4] Recombinant G1 has received the most attention to date, and has demonstrated efficacy in rodent models of Crohn's disease, multiple sclerosis, myasthenia gravis, rheumatoid arthritis, graft vs. host disease, autoimmune uveitis, and T cell mediated hepatitis.[5-8,29-32] A key aspect of G1 and G3 extracellular activity is their non-covalent self-association into quaternary structures with multiple carbohydrate-recognition domains (CRDs). For example, G1 associates into homodimers at relatively high (μM) concentrations.[33] To stabilize its activity in dilute conditions, G1 dimers formed via a polypeptide linker, a synthetic polymer, a leucine zipper coiled-coil forming peptide, or an IgG Fc domain were engineered.[4,34-37] Often, these engineered G1 variants demonstrate a minimum effective dose that is approximately 10-fold lower than that of the wild-type protein. In contrast, G3 is unique among galectins in that it assembles into higher-ordered oligomers (≥2 G3 molecules) upon glycan binding via interactions involving its N-terminal domain.[38] No engineered G3 oligomers with improved activity have been reported. Rather, G3 inhibitors have been developed by treating the wild-type protein with collagenase, which cleaves the N-terminal domain without disrupting the CRD.[39] Likewise, it was recently reported G3 fusion proteins that bind glycans yet lack activity for inducing T cell agglutination, apoptosis, and cytokine secretion because they cannot oligomerize.[40] Together, these examples demonstrate the potential of protein engineering approaches to manipulate G1 and G3 immunomodulatory activity by altering their oligomerization.[41] Despite these efforts, though, existing engineered G1 and G3 variants still have minimum effective doses that are in the low μM range (0.5-5 μM), which is impractical for many therapeutic applications. Described herein, is a way to further decrease the effective dose of G1 and G3 can be to combine them into chimeric multivalent assemblies.

In an aspect, the disclosure relates to a Galectin-1/Galectin-3 (Gal-1/Gal-3) dimer comprising, two monomer polypeptides, wherein each monomer polypeptide comprises, a Galectin-1 (Gal-1) polypeptide; a Galectin-3 (Gal-3) polypeptide; and an alpha helix coil, wherein the alpha helix coil is fused between the Gal-1 polypeptide and the Gal-3 polypeptide, wherein the two monomer polypeptides associate with each other via dimerization at the alpha helix coils to form the Gal-1/Gal-3 dimer.

In some embodiments, one or both of the monomer polypeptides has a sequence that is about 90% to about 100% identical to SEQ ID NO: 3. In some embodiments, one or both of the monomer polypeptides comprises the sequence of SEQ ID NO: 3. In some embodiments, one or both of the monomer polypeptides comprises the sequence of SEQ ID NO: 3 with at least one amino acid substitutions as compared to SEQ ID NO: 3. In some embodiments, the Gal-1 polypeptide has a sequence that is about 80% to about 100% identical to SEQ ID NO: 1. In some embodiments, the Gal-1 polypeptides comprises the sequence of SEQ ID NO: 1. In some embodiments, the Gal-1 polypeptides comprises the sequence of SEQ ID NO: 1 with at least one amino acid substitutions as compared to SEQ ID NO: 1. In some embodiments, the Gal-3 polypeptide has a sequence that is about 80% to about 100% identical to SEQ ID NO: 4. In some embodiments, the Gal-3 polypeptides comprises the sequence of SEQ ID NO: 4. In some embodiments, the Gal-3 polypeptides comprises the sequence of SEQ ID NO: 4 with at least one amino acid substitutions as compared to SEQ ID NO: 4. In some embodiments, the Gal-3 polypeptide has a sequence that is about 80% to about 100% identical to SEQ ID NO: 4 less the underlined and bolded histidine tag (i.e., the sequence as set forth omitting the underlined and bolded amino acid residues). In some embodiments, the Gal-3 polypeptides comprises the sequence of SEQ ID NO: 4 less the underlined and bolded histidine tag (i.e., the sequence as set forth omitting the underlined and bolded amino acid residues). In some embodiments, the Gal-3 polypeptides comprises the sequence of SEQ ID NO: 4 less the underlined and bolded histidine tag (i.e., the sequence as set forth omitting the underlined and bolded amino acid residues) with at least one amino acid substitutions as compared to SEQ ID NO: 4 less the underlined and bolded histidine tag (i.e., the sequence as set forth omitting the underlined and bolded amino acid residues).

In some embodiments, the alpha helix coil has a sequence that is about 80% to about 100% identical to any one of SEQ ID NO: 5. In some embodiments, the alpha helix coil comprises the sequence of SEQ ID NO: 5. In some embodiments, the alpha helix coil comprises the sequence of SEQ ID NO: 5 with at least one amino acid substitutions as compared to SEQ ID NO: 5.

In an aspect, the disclosure relates to a Galectin-1/Galectin-3 (Gal-1/Gal-3) polypeptide capable of dimerizing comprising, a Galectin-1 (Gal-1) polypeptide; a Galectin-3 (Gal-3) polypeptide; and an alpha helix coil, wherein the alpha helix coil is fused between the Gal-1 polypeptide and the Gal-3 polypeptide.

In some embodiments, the Gal-1/Gal-3 polypeptide has a sequence that is about 90% to about 100% identical to SEQ ID NO: 3. In some embodiments, the Gal-1/Gal-3 polypeptide comprises the sequence of SEQ ID NO: 3. In some embodiments, the Gal-1/Gal-3 polypeptide comprises the sequence of SEQ ID NO: 3 with at least one amino acid substitutions as compared to SEQ ID NO: 3. In some embodiments, the Gal-1 polypeptide has a sequence that is about 80% to about 100% identical to SEQ ID NO: 1. In some embodiments, the Gal-1 polypeptides comprises the sequence of SEQ ID NO: 1. In some embodiments, the Gal-1 polypeptides comprises the sequence of SEQ ID NO: 1 with at least one amino acid substitutions as compared to SEQ ID NO: 1. In some embodiments, the Gal-3 polypeptide has a sequence that is about 80% to about 100% identical to SEQ ID NO: 4. In some embodiments, the Gal-3 polypeptides comprises the sequence of SEQ ID NO: 4. In some embodiments, the Gal-3 polypeptides comprises the sequence of SEQ ID NO: 4 with at least one amino acid substitutions as compared to SEQ ID NO: 4. In some embodiments, the Gal-3 polypeptide has a sequence that is about 80% to about 100% identical to SEQ ID NO: 4 less the underlined and bolded histidine tag (i.e., the sequence as set forth omitting the underlined and bolded amino acid residues). In some embodiments, the Gal-3 polypeptides comprises the sequence of SEQ ID NO: 4 less the underlined and bolded histidine tag (i.e., the sequence as set forth omitting the underlined and bolded amino acid residues). In some embodiments, the Gal-3 polypeptides comprises the sequence of SEQ ID NO: 4 less the underlined and bolded histidine tag (i.e., the sequence as set forth omitting the underlined and bolded amino acid residues) with at least one amino acid substitutions as compared to SEQ ID NO: 4 less the underlined and bolded histidine tag (i.e., the sequence as set forth omitting the underlined and bolded amino acid residues).

In some embodiments, the alpha helix coil has a sequence that is about 80% to about 100% identical to SEQ ID NO: 5. In some embodiments, the alpha helix coil comprises the sequence of SEQ ID NO: 5. In some embodiments, the alpha helix coil comprises the sequence of SEQ ID NO: 5 with at least one amino acid substitutions as compared to SEQ ID NO: 5.

In an aspect, the disclosure relates to a Galectin-1/Galectin-3 (Gal-1/Gal-3) polynucleotide comprising, a polynucleotide that encodes a Galectin-1 (Gal-1) polypeptide; a polynucleotide that encodes a Galectin-3 (Gal-3) polypeptide; and a polynucleotide that encodes an alpha helix coil, wherein the polynucleotide that encodes the alpha helix coil is fused in-frame between the polynucleotide that encodes the Gal-1 polypeptide and the polynucleotide that encodes the Gal-3 polypeptide.

In some embodiments, the polynucleotide encodes a Gal-1 polypeptide comprising a sequence that is about 80% to about 100% identical to SEQ ID NO: 1. In some embodiments, the polynucleotide encodes a Gal-1 polypeptide comprising the sequence of SEQ ID NO: 1. In some embodiments, the polynucleotide encodes a Gal-1 polypeptide comprising the sequence of SEQ ID NO: 1 with at least one amino acid substitutions as compared to SEQ ID NO: 1. In some embodiments, the polynucleotide encodes a Gal-3 polypeptide comprising a sequence that is about 80% to about 100% identical to SEQ ID NO: 4. In some embodiments, the polynucleotide encodes a Gal-3 polypeptide comprising the sequence of SEQ ID NO: 4. In some embodiments, the polynucleotide encodes a Gal-3 polypeptide comprising the sequence of SEQ ID NO: 4 with at least one amino acid substitutions as compared to SEQ ID NO: 4. In some embodiments, the polynucleotide encodes a Gal-3 polypeptide comprising a sequence that is about 80% to about 100% identical to SEQ ID NO: 4 less the underlined and bolded histidine tag (i.e., the sequence as set forth omitting the underlined and bolded amino acid residues). In some embodiments, the polynucleotide encodes a Gal-3 polypeptide comprising the sequence of SEQ ID NO: 4 less the underlined and bolded histidine tag (i.e., the sequence as set forth omitting the underlined and bolded amino acid residues). In some embodiments, the polynucleotide encodes a Gal-3 polypeptide comprising the sequence of SEQ ID NO: 4 less the underlined and bolded histidine tag (i.e., the sequence as set forth omitting the underlined and bolded amino acid residues) with at least one amino acid substitutions as compared to SEQ ID NO: 4 less the underlined and bolded histidine tag (i.e., the sequence as set forth omitting the underlined and bolded amino acid residues).

In some embodiments, the polynucleotide encodes an alpha helix coil comprising a sequence that is about 80% to about 100% identical to SEQ ID NO: 5. In some embodiments, the polynucleotide encodes an alpha helix coil comprising the sequence of SEQ ID NO: 5. In some embodiments, the polynucleotide encodes an alpha helix coil comprising the sequence of SEQ ID NO: 5 with at least one amino acid substitutions as compared to SEQ ID NO: 5.

In an aspect, the disclosure relates to a vector comprising, any of the Gal-1/Gal-3 polynucleotides as described herein.

In some embodiments, the Gal-1/Gal-3 polynucleotide is operatively linked to a regulatory polynucleotide.

In an aspect, the disclosure relates to a bacterial cell comprising, any of the polynucleotide sequences as described herein or any of the vectors as described herein.

In an aspect, the disclosure relates to a pharmaceutical formulation comprising, any of the Galectin-1/Galectin-3 (Gal-1/Gal-3) dimers as described herein; and a pharmaceutically acceptable carrier.

In an aspect, the disclosure relates a pharmaceutical formulation comprises a plurality of any of the Galectin-1/Galectin-3 (Gal-1/Gal-3) polypeptides capable of dimerizing as described herein; and a pharmaceutical formulation thereof.

In an aspect, the disclosure relates to a method comprising: administering any of the Galectin-1/Galectin-3 (Gal-1/Gal-3) dimers as described herein or a pharmaceutical formulation thereof to a subject in need thereof.

In some embodiments, the subject in need thereof has inflammatory disease. In some embodiments, the subject in need thereof has an autoimmune disease. In some embodiments, the subject in need thereof has arthritis. In some embodiments, the subject in need thereof has osteoarthritis. In some embodiments, the subject in need thereof has rheumatoid arthritis. In some embodiments, the subject in need thereof has diabetes. In some embodiments, the subject in need thereof has type I diabetes. In some embodiments, the subject in need thereof has multiple sclerosis. In some embodiments, the subject in need thereof has graft versus host disease. In some embodiments, the subject in need thereof has colitis. In some embodiments, the subject in need thereof has uveitis. In some embodiments, the subject in need thereof is rejecting a transplanted organ or tissue.

BRIEF DESCRIPTION OF THE DRAWINGS

Further aspects of the disclosure will be readily appreciated upon review of the Detailed Description of its various aspects and embodiments, described below, when taken in conjunction with the accompanying Drawings.

FIGS. 2A-2C show results that demonstrate the characterization of the physical properties of G1/G3 and G1/G3 dimer. (FIG. 2A) SDS-PAGE gel of G1/G3, G1/G3 dimer, and G1. (FIG. 2B) SEC traces of G1/G3 and G1/G3 dimer. Table in FIG. 2B: approximate molecular weights estimated from SEC elution volume. (FIG. 2C) Dynamic light scattering histograms for G1/G3 and G1/G3 dimer (number-weighted size distribution).

(FIG. 3A) Lactose affinity chromatography traces for of G1, G1-PEG-G1, G1/G3, and G1/G3 dimer. Kinetic turbidity measurements of the formation of insoluble asialofetuin (ASF) aggregates via (FIG. 3B) G1 or G1-PEGG1 and (FIG. 3C) G1/G3 or G1/G3 dimer.

(FIG. 4C) Metabolic activity (normalized to untreated cells) of Jurkat T cells treated with 5 or 0.5 $\mu$M G1, G1-PEG-G1, G1/G3, or G1/G3 dimer for 18 h. * denotes significant difference between concentrations, & denotes significant difference compared to G1/G3 dimer, ^ denotes significant difference compared to untreated control (dashed line). One symbol=$p<0.05$, two symbols=$p<0.01$, three symbols=$p<0.001$, four symbols=$p<0.0001$. Scale bars=50 $\mu$M in (FIG. 4A) and (FIG. 4B).

(FIG. 6A) Kinetic turbidity measurements of the formation of insoluble aggregates in mixtures of media and G1/G3 dimer with or without serum (FBS). (FIG. 6B) Brightfield micrographs of aggregates formed in mixtures of 5 $\mu$M G1/G3 dimer and media with 10% or 1% serum. (FIG. 6C) Turbidity end-point measurements of solutions containing 5 $\mu$M G1/G3 dimer with or without serum and with or without the addition of $\beta$-lactose as a binding inhibitor. (FIG. 6D) Turbidity end-point measurements of solutions containing 5 $\mu$M G1/G3 dimer and different concentrations of serum. In (FIG. 6C), ** denotes $p<0.0001$ compared to all other groups. In (FIG. 6D), ** denotes $p<0.0001$ compared to indicated group. Scale bars=50 $\mu$M.

(FIG. 7C) Metabolic activity (normalized to untreated cells) of Jurkat T cells treated with 5 or 0.5 $\mu$M G1, G1-PEG-G1, or G1/G3 dimer for 18 h. * denotes significant difference between concentrations, & denotes significant difference compared to G1/G3 dimer, ^ denotes significant difference compared to untreated control (dashed line). One symbol=$p<0.05$, two symbols=$p<0.01$, three symbols=$p<0.001$, four symbols=$p<0.0001$. Scale bars=50 $\mu$M in (FIG. 7A) and (FIG. 7B).

(FIG. 11A) Brightfield micrographs of Jurkat T cells after 18 hours treatment with 5 μM G1-GFP. (FIG. 11B) Normalized metabolic activity of Jurkat T cells incubated with G1, G1/G3, and G1-GFP. * $p<0.001$ and ** $p<0.0001$. Scale bar is 50 μM.

DETAILED DESCRIPTION

Figure 1:
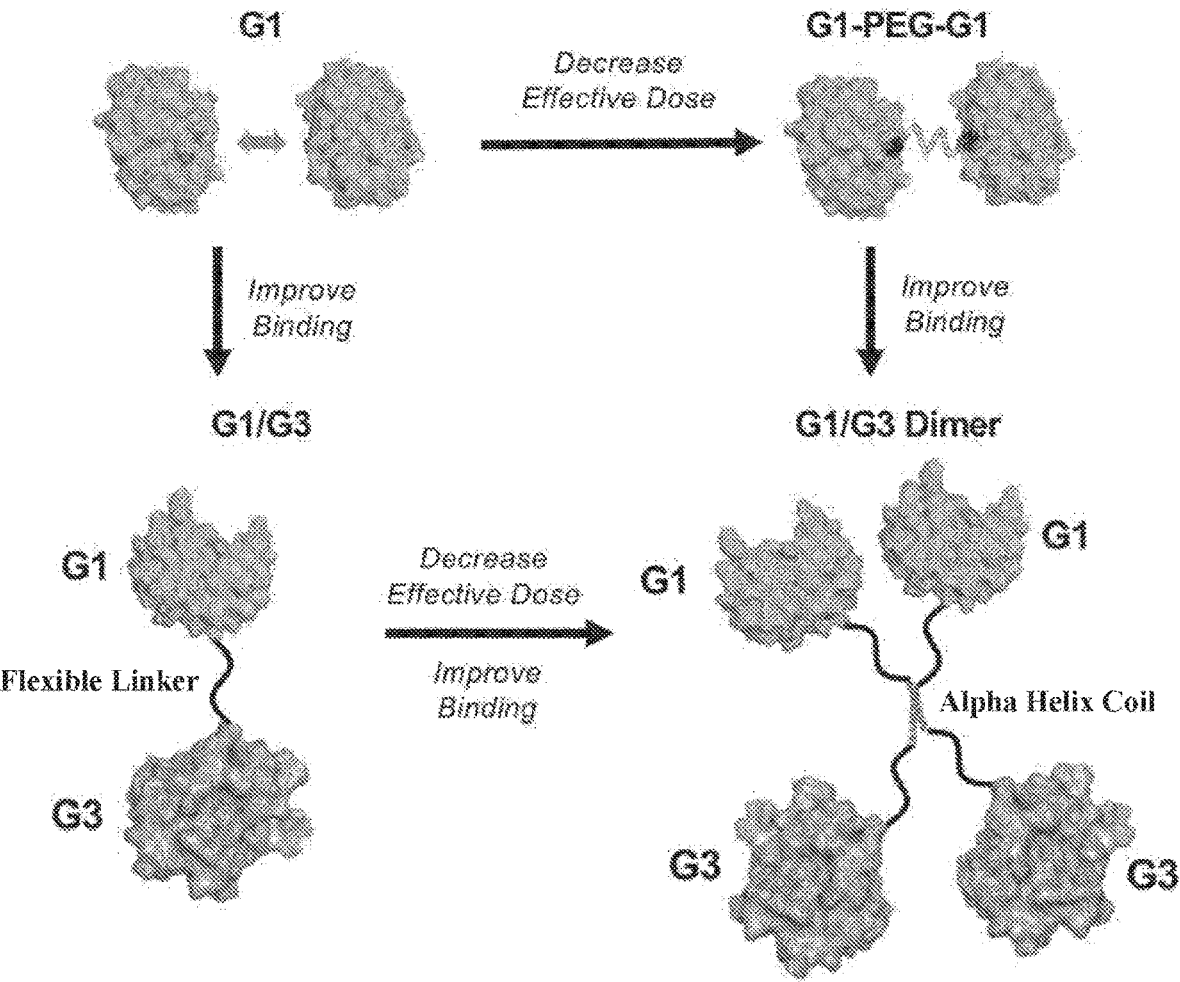
FIG. 1 shows a schematic representation of the wild-type (wt) reversible galectin-1 homodimer ("G1"), a stable G1 homodimer formed by chemical crosslinking with poly (ethylene glycol) ("G1-PEG-G1"), a recombinant fusion of G1 linked to the N-terminus of G3 ("G1/G3"), and a recombinant fusion of G1 linked to G3 via a peptide that forms a two-stranded a-helical coiled-coil ("G1/G3 dimer").

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z' Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "additive effect" refers to an effect arising between two or more molecules, compounds, substances, factors, or compositions that is equal to or the same as the sum of their individual effects.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g., by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intracisternal, intrathecal, intrahepatic, intralesional, and intracranial injections or infusion techniques.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "alpha helix coil," or "a helix" as it may also be referred to, refers to a secondary structure of a protein (e.g., peptide of more than one amino acid residue), which consists of a peptide chain coiled into a right-handed spiral conformation, which conformation is stabilized by hydrogen bonds between the NH and CO groups in the backbone of the peptide.

As used herein, "amphiphilic" can refer to a molecule combining hydrophilic and lipophilic (hydrophobic) properties.

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "chemotherapeutic agent" or "chemotherapeutic" refers to a therapeutic agent utilized to prevent or treat cancer.

As used herein, "concentrated" can refer to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" can refer to an alternative subject or sample used in an experiment for comparison purpose and included to minimize or distinguish the effect of variables other than an independent variable.

As used herein with reference to the relationship between DNA, cDNA, cRNA, RNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "DNA molecule" can include nucleic acids/polynucleotides that are made of DNA.

As used herein, "dose," "unit dose," or "dosage" can refer to physically discrete units suitable for use in a subject, each unit containing a predetermined quantity of the Gal-1/Gal-3 monomer(s) and/or dimer(s) thereof and/or a pharmaceutical formulation thereof calculated to produce the desired response or responses in association with its administration.

As used herein, "effective amount" can refer to the amount of a compound provided herein that is sufficient to effect beneficial or desired biological, emotional, therapeutic, medical, or clinical response of a cell, tissue, system, animal, or human. An effective amount can be administered in one or more administrations, applications, or dosages. The term cam also include within its scope amounts effective to enhance or restore to substantially normal physiological function. "Effective amount" can refer to the amount of a Gal-1/Gal-3 monomer(s) and/or dimer(s) thereof and/or a pharmaceutical formulation thereof described herein that can treat and/or prevent an enzyme deficiency (e.g., a Gal-1 and/or Gal-3 enzyme deficiency), periodontal disease, an autoimmune disease, inflammation, arthritis (e.g., osteoarthritis and rheumatoid arthritis), type 1 diabetes, multiple sclerosis, graft versus host disease, colitis, uveitis, transplant rejection, inflammatory disease and/or a symptom thereof. "Effective amount" can refer to the amount of a Gal-1/Gal-3 dimer and/or pharmaceutical formulation thereof described herein that can affect cell metabolism, decrease cell viability, or direct cell phenotypes. "Effective amount" can refer to modulating a T cell response. "Effective amount" can refer to modulating the balance of different types of T cells, including but not limited to the balance of $T_{h17}/T_{h1}$ to $T_{h2}$. "Effective amount" can refer to modulating the subject's response (e.g., an immune response) to a vaccine, including but not limited to modulating the migration of immune cells (e.g., dendritic cells).

As used herein, "expression" can refer to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, the terms "Fc portion," "Fc region," and the like are used interchangeable herein and can refer to the fragment crystallizable region of an antibody that interacts with cell surface receptors called Fc receptors and some proteins of the complement system. The IgG Fc region is composed of two identical protein fragments that are derived from the second and third constant domains of the IgG antibody's two heavy chains.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

As used herein, "identity," can refer to a relationship between two or more nucleotide or polypeptide sequences, as determined by comparing the sequences. In the art, "identity" can also refers to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," refers to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "lipophilic", as used herein, refers to compounds having an affinity for lipids.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "operatively linked" in the context of recombinant DNA molecules, vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to effect expression or other characteristic of the coding sequence or transcribed non-coding sequence. This same term can be applied to the arrangement of coding sequences, non-coding and/or transcription control elements (e.g., promoters, enhancers, and termination elements), and/or selectable markers in an expression vector. "Operatively linked" can also refer to an indirect attachment (i.e., not a direct fusion) of two or more polynucleotide sequences or polypeptides to each other via a linking molecule (also referred to herein as a linker).

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "overexpressed" or "overexpression" refers to an increased expression level of an RNA and/or protein product encoded by a gene as compared to the level of expression of the RNA or protein product in a normal or control cell. The amount of increased expression as compared to a normal or control cell can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.3, 3.6, 3.9, 4.0, 4.4, 4.8, 5.0, 5.5, 6, 6.5, 7, 7.5, 8.0, 8.5, 9, 9.5, 10, 11, 12, 13, 14, 15, 16, 17, 18, 19, 20, 25, 30, 35, 40, 45, 50, 60, 70, 0, 90, 100 fold or more greater than the normal or control cell.

As used herein, the terms "optional" or "optionally" means that the subsequently described event or circumstance can or cannot occur, and that the description includes instances where said event or circumstance occurs and instances where it does not.

As used herein "peptide" can refer to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "plasmid" refers to a non-chromosomal double-stranded DNA sequence including an intact "replicon" such that the plasmid is replicated in a host cell.

As used herein, "positive control" refers to a "control" that is designed to produce the desired result, provided that all reagents are functioning properly and that the experiment is properly conducted.

As used herein, "preventative" and "prevent" refers to hindering or stopping a disease or condition before it occurs, even if undiagnosed, or while the disease or condition is still in the sub-clinical phase.

"Polymers" are understood to include, but are not limited to, homopolymers, copolymers, such as for example, block, graft, random and alternating copolymers, terpolymers, etc. and blends and modifications thereof.

As used herein, "polypeptides" or "proteins" refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Be, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, "promoter" includes all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "separated" can refer to the state of being physically divided from the original source or population such that the separated compound, agent, particle, or molecule can no longer be considered part of the original source or population.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used interchangeably herein, "subject," "individual," or "patient" can refer to a vertebrate organism, such as a mammal (e.g., human). "Subject" can also refer to a cell, a population of cells, a tissue, an organ, or an organism, preferably to human and constituents thereof.

As used herein, "substantially free" can mean an object species is present at non-detectable or trace levels so as not to interfere with the properties of a composition or process.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g., mass, volume, dosage, concentration, and/or time period) needed to achieve one or more desired result(s). For example, a therapeutically effective amount refers to an amount needed to achieve one or more therapeutic effects.

A "suitable control" is a control that will be instantly appreciated by one of ordinary skill in the art as one that is included such that it can be determined if the variable being evaluated an effect, such as a desired effect or hypothesized effect. One of ordinary skill in the art will also instantly appreciate based on inter alia, the context, the variable(s), the desired or hypothesized effect, what is a suitable or an appropriate control needed.

As used herein, "synergistic effect," "synergism," or "synergy" can refer to an effect arising between two or more molecules, compounds, substances, factors, or compositions that that is greater than or different from the sum of their individual effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, "transforming" when used in the context of engineering or modifying a cell, refers to the introduction by any suitable technique and/or the transient or stable incorporation and/or expression of an exogenous gene in a cell.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a protein deficiency (e.g., a Gal-1 and/or Gal-3 deficiency), periodontal disease, an autoimmune disease, inflammation, arthritis (e.g., osteoarthritis and rheumatoid arthritis), type 1 diabetes, multiple sclerosis, graft versus host disease, colitis, uveitis, transplant rejection, inflammatory disease and/or a symptom thereof. The effect can be therapeutic in terms of a partial or complete cure of a disease, condition, symptom or adverse effect attributed to the disease, disorder, or condition. The term "treatment" as used herein covers any treatment of a protein deficiency (e.g., a Gal-1 and/or Gal-3 deficiency), periodontal disease, an autoimmune disease, inflammation, arthritis (e.g., osteoarthritis and rheumatoid arthritis), type 1 diabetes, multiple sclerosis, graft versus host disease, colitis, uveitis, transplant rejection, inflammatory disease and/or a symptom thereof. in a subject, particularly a human, and can include any one or more of the following: (a) preventing the disease from occurring in a subject which may be predisposed to the disease but has not yet been diagnosed as having it; (b) inhibiting the disease, e.g., arresting its development; and (c) relieving the disease, e.g., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "variant" can refer to a polynucleotide or polypeptide that differs from a reference polynucleotide or polypeptide, but retains essential and/or characteristic properties (structural and/or functional) of the reference polynucleotide or polypeptide. A typical variant of a polypeptide differs in amino acid sequence from another, reference polypeptide. The differences can be limited so that the sequences of the reference polypeptide and the variant are closely similar overall and, in many regions, identical. A variant and reference polypeptide may differ in nucleic or amino acid sequence by one or more modifications at the sequence level or post-transcriptional or post-translational modifications (e.g., substitutions, additions, deletions, methylation, glycosylations, etc.). A substituted nucleic acid may or may not be an unmodified nucleic acid of adenine, thiamine, guanine, cytosine, uracil, including any chemically, enzymatically or metabolically modified forms of these or other nucleotides. A substituted amino acid residue may or may not be one encoded by the genetic code. A variant of a polypeptide may be naturally occurring such as an allelic variant, or it may be a variant that is not known to occur naturally. "Variant" includes functional and structural variants.

As used herein, the term "vector" or is used in reference to a vehicle used to introduce an exogenous nucleic acid sequence into a cell. A vector may include a DNA molecule, linear or circular (e.g., plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

Discussion

Although glycobiology research was first recognized in the early 19$^{th}$ century, researchers are just now beginning to understand the complex role of lectins and glycans within the immune system. Galectins are a family of soluble, beta-galactoside-binding lectins that regulate the phenotype and function of various immune cells during the initiation and resolution of immune responses. For example, galectin-1 (G1) and galectin-3 (G3) are mediators of tumor immunosuppression and fetal-maternal tolerance, regulate autoimmune disease progression, can enhance or inhibit viral infection, and induce pro-inflammatory responses during osteoarthritis.

Extracellular G1 and G3 can act on innate immune cells, including monocytes, macrophages, neutrophils, and dendritic cells, yet it is their influence on T cells that receives the most attention for immunotherapy. G1 and G3 have a variety of diverse of effects on T cells. In light of these diverse effects on T cells, exogenous galectins and engineered variants have been evaluated as therapeutics to regulate adaptive immunity in various contexts. Despite efforts to develop G1- and G3-based therapeutics, efforts using existing engineered G1 and G3 variants still have minimum effective doses that are in the low µM range (e.g., 0.5-5 µM), which is impractical for many therapeutic applications.

With that said, described herein are galectin-1/galectin-3 (Gal-1/Gal-3) multivalent protein complexes and uses thereof. In some aspects, the Gal-1/Gal-3 multivalent protein complex can be composed of a homodimer of two Gal-1/Gal-3 fusion proteins that associate with each other via alpha helix coil linkers contained in each monomer. Each monomer can be composed of a Gal-1/Gal-3 fusion protein where Gal-1 is linked to the Gal-3 via an alpha helix coil linker. The Gal-1/Gal-3 multivalent protein complexes described herein can be administered to a subject in need thereof. In some aspects, the subject in need thereof can have an inflammatory disease or disorder. In some aspects, the inflammatory disease or disorder is arthritis, such as osteoarthritis. An advantage of the Gal-1/Gal-3 multivalent protein complexes herein is that, unexpectedly, the Gal-1/Gal-3 multivalent protein complexes have extracellular activities not achieved by Gal-1 alone, Gal-3 alone, or a Gal-1/Gal-3 fusion protein alone. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Gal-1/Gal-3 Multivalent Protein Complexes

Described herein are Galectin-1/Galectin-3 (Gal-1/Gal-3) multivalent protein complexes that can be composed of a Galectin-1/Galectin-3 (Gal-1/Gal-3) dimer. The Gal-1/Gal-3 dimer can be composed of two monomer polypeptides. Each monomer polypeptide can be composed of a Galectin-1 (Gal-1) polypeptide, a Galectin-3 (Gal-3) polypeptide, and a linker consisting of or comprising an alpha helix coil (e.g., optionally including a linker peptide on one or both sides of an alpha helix coil dimerization domain) or other dimerization domain. In some embodiments, either or both of the Gal-1 and/or Gal-3 polypeptide is a mammalian polypeptide (e.g., from a primate, a human, or other mammal) or a fragment or variant thereof. The linker can be fused between the Gal-1 polypeptide and the Gal-3 polypeptide. In some embodiments, the linker joins the N-terminus of a Gal-3 polypeptide to the C-terminus of a Gal-1 polypeptide. In some embodiments, the linker joins the C-terminus of a Gal-3 polypeptide to the N-terminus of a Gal-1 polypeptide. The two monomer polypeptides can associate with each other via dimerization at the alpha helix coils to form the Gal-1/Gal-3 dimer. In some aspects, the Gal-1/Gal-3 dimer can be a homodimer, which refers to a dimer in which each monomer polypeptide has an identical amino acid sequence to the other. In some aspects, the Gal-1/Gal-3 dimer can be a heterodimer, which refers to a dimer in which each monomer polypeptide has different amino acid sequence as compared to the other. Each monomer can optionally contain on or more purification and/or identification tags (e.g., histidine (His) tags, FLAG tags, bioactive or enzymatic polypeptides (e.g., fluorescent proteins, luciferase proteins, beta-galactosidase proteins)). Other suitable tags will be appreciated by those of skill in the art. The reporter/purification tag can be positioned at the N-terminus and/or C-terminus of the monomer polypeptide. In other aspects, the reporter/purification tag can be fused in-frame at any suitable location between the N-terminus C-terminus of the monomer polypeptide. A suitable position is considered as a position between the N-terminus that and C-terminus that does not significantly impact the ability of dimer formation or other activity of the Gal-1, Gal-3, Gal-1 and Gal-3, and/or the monomer polypeptide. In some embodiments, any of the monomer(s) and/or dimers comprises the polypeptides described herein without purification and/or identification tags. In some embodiments, the purification and/or identification tags are shown in SEQ ID NO: 2-4 as underlined and bolded.

Variants of Galectins are also contemplated by the disclosure. Variants of Galectins (e.g., Gal-1 (i.e., G1), Gal-3 (i.e., G3)) are proteins which may vary in sequence or origin, but which have analogous or homologous functions. Variants may be the result of intentional modification or by naturally occurring variances (e.g., mutations). Variants of Gal-1 and/or Gal-3 may vary in percent identity (i.e., % identity). In some embodiments, the variants have 60% (e.g., 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more) identity to Gal-1 or Gal-3, respectively. In some embodiments, a Gal-1 variant is substituted for Gal-1 in the monomer(s) and/or dimers of the instant disclosure. In some embodiments, the Gal-1 variant is one or more of the following: LGALS1, 14 kDa laminin-binding protein; HLBP14; 14 kDa lectin; Beta-galactoside-binding lectin L-14-I; Galaptin; HBL; HPL; Lactose-binding lectin 1; Lectin galactoside-binding soluble 1; Putative MAPK-activating protein PM12; and S-Lac lectin 1. In some embodiments, a Gal-3 variant is substituted for Gal-3 in the monomer(s) and/or dimers of the instant disclosure. In some embodiments, the Gal-3 variant is one or more of the following: LGALS3; 35 kDa lectin; Carbohydrate-binding protein 35; CBP 35; Galactose-specific lectin 3; Galactoside-binding protein; GALBP; IgE-binding protein; L-31; Laminin-binding protein; Lectin L-29; and Mac-2 antigen.

In some aspects, one or both of the monomer polypeptides comprises a sequence that is about 90% to about 100% identical (e.g., 90%, 92%, 93%, 94%, 95%, 96%, 97%, 98%, 99%, 99.5%, 99.6%, 99.7%, 99.8%, 99.9% identical, or more) to SEQ ID NO: 3. In some aspects, one or both of the G1/G3 dimer comprises a sequence that is about 90% to about 100% identical (e.g., 90%, 92%, 93%, 94%, 95%, 96%, 97%, 98%, 99%, 99.5%, 99.6%, 99.7%, 99.8%, 99.9% identical, or more) to SEQ ID NO: 3. In some aspects, one or both of the monomer polypeptides comprises a sequence that is about 90% to about 100% identical (e.g., 90%, 92%, 93%, 94%, 95%, 96%, 97%, 98%, 99%, 99.5%, 99.6%, 99.7%, 99.8%, 99.9% identical, or more) to SEQ ID NO: 3 less the underlined and bolded histidine tag (i.e., the sequence as set forth omitting the underlined and bolded amino acid residues). In some aspects, one or both of the G1/G3 dimer comprises a sequence that is about 90% to about 100% identical (e.g., 90%, 92%, 93%, 94%, 95%, 96%, 97%, 98%, 99%, 99.5%, 99.6%, 99.7%, 99.8%, 99.9% identical, or more) to SEQ ID NO: 3 less the underlined and bolded histidine tag (i.e., the sequence as set forth omitting the underlined and bolded amino acid residues). In some embodiments, the Gal-1 polypeptide comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 1. In some embodiments, the Gal-3 polypeptide comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 4. In some embodiments, the Gal-3 polypeptide comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 4 less the underlined and bolded histidine tag (i.e., the sequence as set forth omitting the underlined and bolded amino acid residues). In some embodiments, the alpha helix coil comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 5. In some embodiments, the alpha helix coil (e.g., the dimerization domain) comprises a sequence of SEQ ID NO: 5. In some embodiments, the alpha helix coil comprises a dimerization sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 9. In some embodiments, the alpha helix coil comprises a dimerization sequence of SEQ ID NO: 9. In some embodiments, the dimerization sequence is flanked on one or both ends by a linker sequence. In some embodiments, the linker sequence comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 10 or SEQ ID NO: 11. In some embodiments, the linker sequence comprises a sequence of SEQ ID NO: 10 or SEQ ID NO: 11. Also described herein are monomer polypeptides that are capable of dimerizing, where each monomer can be as previously described.

In some aspects, one or both of the monomer polypeptides comprises a sequence that has at least one amino acid substitution (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or more) as compared to SEQ ID NO: 3. In some embodiments, the Gal-1 polypeptide comprises a sequence that has at least one amino acid substitution (e.g., 1, 2, 3, 4, 5, 6, 7, 8, 9, 10, 11, 12, 13, 14, 15, 16, or more) as compared to SEQ ID NO: 1. In some embodiments, the Gal-3 polypeptide comprises a sequence that has at least one amino acid substitution (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or more) as compared to SEQ ID NO: 4. In some embodiments, the Gal-3 polypeptide comprises a sequence that has at least one amino acid substitution (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or more) as compared to SEQ ID NO: 4 less this underlined and bolded histidine tag. In some embodiments, the alpha helix coil comprises a sequence that has at least one amino acid substitution (e.g., 1, 2, 3, 4, 5, 6, 7, 8, 9, 10, 11, 12, or more) as compared to SEQ ID NO: 5 or SEQ ID NO: 9. Also described herein are monomer polypeptides that are capable of dimerizing, where each monomer can be as previously described. In some embodiments, at least 1 (e.g., 1, 2, 3, 4, or more) of the surface-exposed cysteine amino acid residues are mutated (e.g., substituted, changed) to serine residues. In some embodiments, at least 2 (e.g., 2, 3, 4, or more) of the surface-exposed cysteine amino acid residues are mutated (e.g., substituted, changed) to serine residues. In some embodiments, at least 3 (e.g., 3, 4, or more) of the surface-exposed cysteine amino acid residues are mutated (e.g., substituted, changed) to serine residues. In some embodiments, at least 4 (e.g., 4, or more) of the surface-exposed cysteine amino acid residues are mutated (e.g., substituted, changed) to serine residues. In some embodiments, Gal-3 is truncated. In some embodiments, Gal-3 is truncated in the unstructured domain. In some embodiments, the unstructured domain comprises the first 115 amino acids reading from the N-terminus. In some embodiments, the truncation does not affect Gal-3's sugar-binding properties. In some embodiments, the truncation affects, but does not eliminate Gal-3's sugar binding properties. In some embodiments, Gal-3 is truncated at least 1 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, or more) amino acid at the N-terminus of the peptide.

In some aspects, one or both of the monomer polypeptides comprises a sequence that has at least one amino acid insertion or deletion (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or more) as compared to SEQ ID NO: 3. In some embodiments, the Gal-1 polypeptide comprises a sequence that has at least one amino acid insertion or deletion (e.g., 1, 2, 3, 4, 5, 6, 7, 8, 9, 10, 11, 12, 13, 14, 15, 16, or more) as compared to SEQ ID NO: 1. In some embodiments, the Gal-3 polypeptide comprises a sequence that has at least one amino acid insertion or deletion (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or more) as compared to SEQ ID NO: 4. In some embodiments, the Gal-3 polypeptide comprises a sequence that has at least one amino acid insertion or deletion (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or more) as compared to SEQ ID NO: 4 less the underlined and bolded histidine tag (i.e., the sequence as set forth omitting the underlined and bolded amino acid residues). In some embodiments, the alpha helix coil comprises a sequence that has at least one amino acid insertion or deletion (e.g., 1, 2, 3, 4, 5, 6, 7, 8, 9, 10, 11, 12, or more) as compared to SEQ ID NO: 5. In some embodiments, the alpha helix coil dimerization sequence comprises a sequence that has at least one amino acid insertion or deletion (e.g., 1, 2, 3, 4, 5, 6, 7, or more) as compared to SEQ ID NO: 9.

Gal-1/Gal-3 Monomer Polynucleotides and Recombinant Vectors

Also described herein are polynucleotides that can be capable of encoding a Gal-1/Gal-3 monomer as described herein. In some aspects, the Gal-1/Gal-3 polynucleotide is composed of a polynucleotide that encodes a Galectin-1 (Gal-1) polypeptide, a polynucleotide that encodes a Galectin-3 (Gal-3) polypeptide; and a polynucleotide that encodes an alpha helix coil. In aspects, the polynucleotide that encodes the alpha helix coil can be fused in-frame between the polynucleotide that encodes the Gal-1 polypeptide and the polynucleotide that encodes the Gal-3 polypeptide. In some aspects, a polynucleotide encodes a Gal-1 polypeptide comprising a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 1. In some embodiments, the polynucleotide encoding a Gal-1 polypeptide comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 7. In some embodiments, the polynucleotide encoding a Gal-1 polypeptide comprises SEQ ID NO: 7. In some aspects, a polynucleotide encodes a Gal-3 polypeptide having a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 4. In some aspects, a polynucleotide encodes a Gal-3 polypeptide having a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 4 less the underlined and bolded histidine tag (i.e., the sequence as set forth omitting the underlined and bolded amino acid residues). In some embodiments, the polynucleotide encoding a Gal-3 polypeptide comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 8. In some embodiments, the polynucleotide encoding a Gal-1 polypeptide comprises SEQ ID NO: 8. In some embodiments, the polynucleotide encoding a Gal-1/Gal-3 dimer polypeptide comprises a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 6. In some embodiments, the polynucleotide encoding a Gal-1/Gal-3 polypeptide comprises SEQ ID NO: 6. In some embodiments, the polynucleotide encoding a Gal-1/Gal-3 dimer polypeptide comprises a sequence that encodes a polypeptide which is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 3. In some aspects, a polynucleotide encodes an alpha helix coil has a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 5. In some aspects, a polynucleotide encodes an alpha helix coil dimerization sequence that has a sequence that is about 80% to about 100% identical (e.g., 80%, 82%, 83%, 84%, 85%, 86%, 87%, 88%, 89%, 90%, 92%, 93%, 94%, 95%, 96%, 97%, 98%, 99%, 99.5%, 99.6%, 99.7%, 99.8%, 99.9% identical, or more) to SEQ ID NO: 9.

In some aspects, a polynucleotide that can be capable of encoding a Gal-1/Gal-3 monomer polypeptide as described herein can be incorporated into a suitable expression vector. The skilled artisan will readily be able to appreciate the properties and appropriate selection of suitable vectors. In some embodiments, any suitable vector is chosen by the skilled artisan. In some embodiments, an *Escherichia coli* (i.e., *E. coli*) vector is used, for example, pET *E. coli* expression vectors (NOVAGEN™). The expression vector can contain one or more regulatory sequences or one or more other sequences used to facilitate the expression of the Gal-1/Gal-3 monomer encoding polynucleotide. The skilled artisan will readily be able to appreciate the properties and appropriate selection of suitable regulatory sequences. In some embodiments, any suitable regulatory sequence is chosen by the skilled artisan. In some embodiments, an T7 regulatory sequence is used. The expression vector can contain one or more regulatory sequences or one or more other sequences used to facilitate the replication of the Gal-1/Gal-3 monomer polypeptide expression vector, such as in a viral-based expression system. The expression vector can be suitable for expressing the Gal-1/Gal-3 monomer polypeptide in a bacterial cell. In other embodiments, the expression vector can be suitable for expressing the Gal-1/Gal-3 monomer polypeptide in a yeast cell. In further embodiments, the expression vector can be suitable for expressing the Gal-1/Gal-3 monomer polypeptide in a plant cell. In other embodiments, the expression vector can be suitable for expressing the Gal-1/Gal-3 monomer polypeptide in a mammalian cell. In another embodiment, the vector can be suitable for expressing the Gal-1/Gal-3 monomer polypeptide in a fungal cell. In further embodiments, the vector can be suitable for expressing the Gal-1/Gal-3 monomer polypeptide in an insect cell. Suitable expression vectors are generally known to those of ordinary skill in the art.

Protein Production

The Gal-1/Gal-3 proteins described herein can be produced in a suitable in vitro expression system such as bacterial production system, yeast system, insect system, or mammalian cell system. Such systems can include growing a population of bacterial, yeast, or mammalian cells that express one or more vectors that include a DNA encoding one or more Gal-1/Gal-3 monomer polypeptides described herein. The cells can produce Gal-1/Gal-3 monomer polypeptides and/or dimers thereof and, in some embodiments, secrete the produced protein into the cell media. After the Gal-1/Gal-3 monomer and/or dimer(s) have been produced, the Gal-1/Gal-3 monomer and/or dimer(s) can be harvested from the cell culture media and/or by lysing the cells to release produced protein contained within the cells.

Pharmaceutical Formulations

Also within the scope of this disclosure are pharmaceutical formulations containing a Gal1/Gal3 monomer polypeptide and/or a Gal-1/Gal-3 dimer as described herein. In some embodiments, the pharmaceutical formulations contain a therapeutically effective amount of a Gal1/Gal3 monomer polypeptide and/or a Gal-1/Gal-3 dimer as described herein. The pharmaceutical formulations described herein can be administered to a subject in need thereof. The subject in need thereof can have an enzymatic deficiency, periodontal disease, and/or autoimmune disease, inflammation, inflammatory disease and/or a symptom thereof. In other embodiments, the Gal-1/Gal-3 monomer polypeptides and/or dimers thereof can be used in the manufacture of a medicament for the treatment or prevention of a protein deficiency, periodontal disease, an autoimmune disease, inflammation, inflammatory disease and/or a symptom thereof. In some embodiments, the subject in need thereof can have arthritis. In some aspects, the arthritis is osteoarthritis. In some embodiments, the arthritis is rheumatoid arthritis. In some embodiments, the subject can have type 1 diabetes. In some embodiments, the subject can have multiple sclerosis. In some embodiments, the subject can have graft versus host disease. In some embodiments, the subject can have colitis. In some embodiments, the subject can have uveitis. In some embodiments, the subject can have transplant rejection. The subject in need thereof can be receiving a vaccine.

To practice any of the methods disclosed herein, an effective amount of the composition described above can be administered to a subject (e.g., a human) in need of the treatment via a suitable route (as discussed herein below). In some embodiments, the subject is a mammal. In some embodiments, the subject is a human.

Pharmaceutically Acceptable Carriers and Auxiliary Ingredients and Agents

The pharmaceutical formulations described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of a Gal-1/Gal-3 monomer polypeptides and/or dimers thereof described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g., melatonin and thyroxine), small peptide hormones and protein hormones (e.g., thyrotropin-releasing hormone, vasopressin, insulin, growth hormone, luteinizing hormone, follicle-stimulating hormone, and thyroid-stimulating hormone), eicosanoids (e.g., arachidonic acid, lipoxins, and prostaglandins), and steroid hormones (e.g., estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g., IL-2, IL-7, and IL-12), cytokines (e.g., interferons (e.g., IFN-$\alpha$, IFN-$\beta$, IFN-$\epsilon$, IFN-$\kappa$, IFN-$\omega$, and IFN-$\gamma$), granulocyte colony-stimulating factor, and imiquimod), chemokines (e.g., CCL3, CCL26 and CXCL7), cytosine phosphate-guanosine, oligodeoxynucleotides, glucans, antibodies, and aptamers).

Suitable antipyretics include, but are not limited to, nonsteroidal anti-inflammants (e.g., ibuprofen, naproxen, ketoprofen, and nimesulide), aspirin and related salicylates (e.g., choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g., alprazolam, bromazepam, chlordiazepoxide, clonazepam, clorazepate, diazepam, flurazepam, lorazepam, oxazepam, temazepam, triazolam, and tofisopam), serotenergic antidepressants (e.g., selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g., ibuprofen, naproxen, ketoprofen, and nimesulide), COX-2 inhibitors (e.g., rofecoxib, celecoxib, and etoricoxib), opioids (e.g., morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g., choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g., ibuprofen, naproxen, ketoprofen, and nimesulide), COX-2 inhibitors (e.g., rofecoxib, celecoxib, and etoricoxib), and immune selective anti-inflammatory derivatives (e.g., submandibular gland peptide-T and its derivatives).

Suitable anti-histamines include, but are not limited to, H1-receptor antagonists (e.g., acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g., cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g., nitazoxanide, paromomycin, metronidazole, tinidazole, chloroquine, miltefosine, amphotericin b, and iodoquinol), aminoglycosides (e.g., paromomycin, tobramycin, gentamicin, amikacin, kanamycin, and neomycin), anthelmintics (e.g., pyrantel, mebendazole, ivermectin, praziquantel, abendazole, thiabendazole, oxamniquine), antifungals (e.g., azole antifungals (e.g., itraconazole, fluconazole, posaconazole, ketoconazole, clotrimazole, miconazole, and voriconazole), echinocandins (e.g., caspofungin, anidulafungin, and micafungin), griseofulvin, terbinafine, flucytosine, and polyenes (e.g., nystatin, and amphotericin b), antimalarial agents (e.g., pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g., aminosalicylates (e.g., aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g., amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g., doripenem, meropenem, ertapenem, and cilastatin/imipenem), cephalosporins (e.g., cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g., vancomycin, dalbavancin, oritavancin, and telvancin), glycylcyclines (e.g., tigecycline), leprostatics (e.g., clofazimine and thalidomide), lincomycin and derivatives thereof (e.g., clindamycin and lincomycin), macrolides and derivatives thereof (e.g., telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaillin, dicloxacillin, and nafcillin), quinolones (e.g., lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g., sulfamethoxazole/trimethoprim, sulfasalazine, and sulfasoxazole), tetracyclines (e.g., doxycycline, demeclocycline, minocycline, doxycycline/salicyclic acid, doxycycline/omega-3 polyunsaturated fatty acids, and tetracycline), and urinary anti-infectives (e.g., nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Effective Amounts of the Gal-1/Gal-3 Monomers, Dimers, and Auxiliary Agents

As discussed elsewhere herein, an advantage of the Gal-1/Gal-3 is that the activity is increased such that a minimum effective amount can be provided while retaining its activity and effect. The pharmaceutical formulations described herein can contain a therapeutically effective amount and/or a minimum effective amount of a Gal-1/Gal-3 dimer. In some embodiments, the pharmaceutical formulations are formulated such that the Gal-1/Gal-3 monomers exist in their monomeric state until right before use where they dimerize. The therapeutically effective amount of the Gal-1/Gal-3 dimer can range from about 1 pg to about 10 g. In some embodiments, the therapeutically effective amount of the Gal-1/Gal-3 dimer thereof can range from about 10 nL to about 10 mL. In some embodiments, the therapeutically effective amount of the Gal-1/Gal-3 dimer can range from about 10 nL to about 1 µL. In some aspects, the therapeutically effective amount of the Gal-1/Gal-3 dimer can range from about 1 ng to about 10 mg per injection, if administered via injection. In some embodiments, the therapeutically effective amount of the Gal-1/Gal-3 dimer thereof can range from about 1 mg/kg to about 10 mg/kg. In further embodiments, the therapeutically effective amount of the Gal-1/Gal-3 dimer can range from 1 ng/g bodyweight to about 1 mg/g bodyweight. In some embodiments, the therapeutically effective amount of the Gal-1/Gal-3 dimer can be from about 1 to about 2 micrograms per injection, such as for a systemically administered injection. In additional embodiments, the therapeutically effective amount can be about 200 to about 300 µL per injection, such as for a systemically administered injection. In some embodiments, the therapeutically effective amount can be about 5 ng/µL, such as for systemic injections. For some embodiments, the therapeutically effective amount can be about 0.1 to about 1.5 µg per 5 g of bodyweight. In some embodiments, the therapeutically effective amount can be from about 10 µg to about 1000 µg per kg of bodyweight. In some embodiments the therapeutically effective amount can be about 0.4 mg/kg to about 4 mg/kg.

In embodiments where there is an auxiliary active agent contained in the pharmaceutical formulation in addition to the Gal-1/Gal-3 dimer and/or monomer(s), the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intracisternal intrathecal, intravitreal, intracerebral, gingival, subgingival, intracerebroventricular, subcutaneous, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the Gal-1/Gal-3 dimer and/or monomer(s) and/or auxiliary agent. The oral dosage form can be administered to a subject in need thereof.

Where appropriate, the dosage forms described herein can be microencapsulated. The dosage form can also be prepared to prolong or sustain the release of any ingredient. In some embodiments, the Gal-1/Gal-3 dimer and/or monomer(s) can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, Gal-1/Gal-3 dimer and/or monomer(s) and/or auxiliary agent can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the Gal-1/Gal-3 monomers, dimers thereof can be in a dosage form adapted for inhalation is in a particle-size-reduced form that is obtained or obtainable by micronization. In some embodiments, the particle size of the size reduced (e.g., micronized) compound or salt or solvate thereof, is defined by a D50 value of about 0.5 microns to about 10 microns (e.g., 0.5, 0.6, 0.7, 0.8, 0.9, 1.0, 1.5, 2.0, 3.0, 4.0, 5.0, 7.0, 10 microns) as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g., the Gal-1/Gal-3 dimer and/or monomer(s) and/or auxiliary agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the Gal-1/Gal-3 dimer and/or monomer(s) and/or auxiliary agent, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g., metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a Gal-1/Gal-3 dimer and/or monomer(s) and/or auxiliary agent. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, 5, 6, 7, 8, or more times daily, in which 1, 2, 3, or more doses are delivered each time.

For some dosage forms suitable and/or adapted for inhaled administration, the pharmaceutical formulation is a dry powder inhalable formulation. In addition to the Gal-1/Gal-3 dimer(s) and/or monomer(s), the pharmaceutical formulation containing the Gal-1/Gal-3 dimer and/or monomer(s) and/or auxiliary agent, such a dosage form can contain a powder base such as lactose, glucose, trehalose, manitol, and/or starch. In some of these embodiments, the Gal-1/Gal-3 dimer(s) and/or monomer(s) and/or auxiliary agent can be in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the Gal-1/Gal-3 dimer and/or monomer(s) and/or auxiliary agent described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g., intravenous, intraperitoneal, subcutaneous, intramuscular, intradermal, intraosseous, epidural, intracardiac, intraarticular, intracavernous, gingival, subginigival, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the Gal-1/Gal-3 dimer and/or monomer(s) and/or auxiliary agent per unit dose. In some embodiments, the predetermined amount of the Gal-1/Gal-3 dimer and/or monomer(s) is an amount effective to treat or prevent an enzymatic deficiency, an immune dysfunction disease, inflammatory disease, arthritis (including but not limited to osteoarthritis and rheumatoid arthritis), periodontal disease and/or a symptom thereof. In some embodiments, the predetermined amount is an amount effective to modulate a T cell response in a subject. In some embodiments the predetermined amount is an amount effective to modulate the balance of different types of T cells, including but not limited to, the balance of $T_{h17}/T_{h1}$ to $T_{h2}$. In some embodiments, the effective amount can be effective to modulate the subject's response (e.g., an immune response) to a vaccine, including but not limited to, modulating the migration of immune cells (e.g., dendritic cells). In some embodiments, the predetermined amount of the Gal-1/Gal-3 dimer and/or monomer(s) and/or auxiliary agent can be an appropriate fraction of the therapeutically effective amount of the active ingredient (e.g., Gal-1/Gal-3 dimer and/or monomer(s) and/or auxiliary agent). Such unit doses may therefore be administered once or more than once a day. Such pharmaceutical formulations may be prepared by any of the methods well known in the art.

Methods of Using the Gal-1/Gal-3 Dimers and Monomers

The Gal-1/Gal-3 dimer and/or monomer(s) and pharmaceutical formulations thereof described herein can be used for the treatment and/or prevention of a disease, disorder, syndrome, or a symptom thereof in a subject. In some embodiments Gal-1/Gal-3 dimer and/or monomer(s) and pharmaceutical formulations thereof described herein can be used to treat and/or prevent a protein deficiency (e.g., a Gal-1 and/or Gal-3 deficiency), periodontal disease, an autoimmune disease, inflammation, inflammatory disease and/or a symptom thereof. In some embodiments, the subject in need thereof can have arthritis. In some aspects, the arthritis is osteoarthritis. In some embodiments, the arthritis is rheumatoid arthritis. In some embodiments, the subject can have type 1 diabetes. In some embodiments, the subject can have multiple sclerosis. In some embodiments, the subject can have graft versus host disease. In some embodiments, the subject can have colitis. In some embodiments, the subject can have uveitis. In some embodiments, the subject can have transplant rejection.

An amount of the Gal-1/Gal-3 dimer and/or monomer(s) and pharmaceutical formulations thereof described herein can be administered to a subject in need thereof one or more times per day, week, month, or year. In some embodiments, the amount administered can be the therapeutically effective amount of the Gal-1/Gal-3 dimer and/or monomer(s) and pharmaceutical formulations thereof. For example, the Gal-1/Gal-3 dimer and/or monomer(s) and pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, 6, or more. In further embodiments, the Gal-1/Gal-3 dimer and/or monomer(s) and pharmaceutical formulations thereof can be administered one or more times per week, such as 1, 2, 3, 4, 5, 6, or more times per week. In other embodiments, the Gal-1/Gal-3 dimer and/or monomer(s) and pharmaceutical formulations thereof can be administered one or more times per month, such as 1 to 5 times (e.g., 1, 2, 3, 4, 5 times) per month. In still further embodiments, the Gal-1/Gal-3 dimer and/or monomer(s) and pharmaceutical formulations thereof can be administered one or more times per year, such as 1 to 11 times (e.g., 1, 2, 3, 4, 5, 6, 7, 8, 9, 10, 11, or more times) per year.

The Gal-1/Gal-3 dimer and/or monomer(s) and pharmaceutical formulations thereof can be co-administered with a secondary agent (e.g., an auxiliary agent) by any convenient route. The secondary agent can be a separate compound and/or formulation from the Gal-1/Gal-3 dimer and/or monomer(s) and pharmaceutical formulations thereof. In some embodiments, the secondary agent is an auxiliary agent that is in addition to an auxiliary agent already present in the Gal-1/Gal-3 dimer and/or monomer pharmaceutical formulation. The secondary agent can be administered simultaneously with the Gal-1/Gal-3 dimer and/or monomer(s) and pharmaceutical formulations thereof. The secondary agent can be administered sequentially with the Gal-1/Gal-3 dimer and/or monomer(s) and pharmaceutical formulations thereof. The secondary agent can have an additive or synergistic effect to the Gal-1/Gal-3 dimer and/or monomer(s) and pharmaceutical formulations thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Exemplary compounds within each of these categories are presented elsewhere herein.

In embodiments where the Gal-1/Gal-3 dimer and/or monomer(s) and pharmaceutical formulations thereof are simultaneously co-administered with a secondary agent, the Gal-1/Gal-3 dimer and/or monomer(s) and pharmaceutical formulations thereof can be administered to the subject at substantially the same time as the secondary agent. As used in this context "substantially the same time" refers to administration of Gal-1/Gal-3 dimer and/or monomer(s) and pharmaceutical formulations thereof and a secondary agent where the period of time between administration of the Gal-1/Gal-3 dimer and/or monomer(s) and pharmaceutical formulations thereof and the secondary agent is between 0 and 10 minutes (e.g., 0, 1, 2, 3, 4, 5, 6, 7, 8, 9, 10 minutes).

In embodiments where the Gal-1/Gal-3 dimer and/or monomer(s) and pharmaceutical formulations thereof is/are sequentially co-administered with a secondary agent, the Gal-1/Gal-3 dimer and/or monomer(s) and pharmaceutical formulations thereof can be administered first, and followed by administration of the secondary agent after a period of time. In other embodiments where the Gal-1/Gal-3 dimer and/or monomer(s) and pharmaceutical formulations thereof is/are sequentially co-administered with a secondary agent, the secondary agent can be administered first, and followed by administration of the Gal-1/Gal-3 dimer and/or monomer(s) and pharmaceutical formulations thereof after a period of time. The period of time between administration of the Gal-1/Gal-3 dimer and/or monomer(s) and pharmaceutical formulations thereof and the secondary agent can range from 10 minutes to about 96 hours. In some embodiments, the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amounts, including effective and minimum effective amounts, of the Gal-1/Gal-3 dimer and/or monomer(s) and pharmaceutical formulations thereof that can be administered are described elsewhere herein. The amount of the secondary agent will vary depending on the secondary agent. The amount of the secondary agent can be a therapeutically effective amount. In some embodiments, the effective amount of the secondary agent ranges from 0.001 micrograms to about 1 milligram. In other embodiments, the amount of the secondary agent can range from about 0.01 IU to about 1000 IU. In further embodiments, the amount of the secondary agent can range from 0.001 mL to about 1 mL. In yet other embodiments, the amount of the secondary agent can range from about 1% w/w to about 50% w/w of the total pharmaceutical formulation. In additional embodiments, the amount of the secondary agent can range from about 1% v/v to about 50% v/v of the total pharmaceutical formulation. In still other embodiments, the amount of the secondary agent can range from about 1% w/v to about 50% w/v of the total secondary agent composition or pharmaceutical formulation.

In some embodiments, the Gal-1/Gal-3 dimer and/or monomer(s) and pharmaceutical formulations thereof can be administered to a patient via an injection. Suitable methods of injection include, but are not limited to, intravenous, intraperitoneal, subcutaneous, intramuscular, intradermal, intraosseous, epidural, intracardiac, intraarticular, intracavernous, intrathecal, intravitreal, intracerebral, gingival, subginigival, intranodal, and intracerebroventricular injection. Other suitable methods of administering the Gal-1/Gal-3 dimer and/or monomer(s) and pharmaceutical formulations thereof include, but are not limited to, topical, transdermal, nasal, or oral delivery. In some embodiments, the dosage of Gal-1/Gal-3 dimer and/or monomer(s) and pharmaceutical formulations thereof ranges from about 0.01 μg/g body-weight to about 10 mg/g bodyweight.

In some aspects, the disclosure relates to a method of using the Gal-1/Gal-3 dimer and/or monomer(s) of the disclosure. In some embodiments, the method comprises, administering the Gal-1/Gal-3 dimer and/or monomer(s) of the disclosure are to a subject. In some embodiments, the subject has an indication (e.g., disease, disorder) as dis-closed herein. In some embodiments, the Gal-1/Gal-3 dimer and/or monomer(s) of the disclosure are administered to a subject in need thereof. In some embodiments, the indication (e.g., disease, disorder) is a protein deficiency (e.g., a Gal-1 and/or Gal-3 deficiency), periodontal disease, an autoim-mune disease, inflammation, inflammatory disease and/or a symptom thereof. In some embodiments, the subject in need thereof can have arthritis. In some aspects, the arthritis is osteoarthritis. In some embodiments, the arthritis is rheu-matoid arthritis. In some embodiments, the subject can have type 1 diabetes. In some embodiments, the subject can have multiple sclerosis. In some embodiments, the subject can have graft versus host disease. In some embodiments, the subject can have colitis. In some embodiments, the subject can have uveitis. In some embodiments, the subject can have transplant rejection. In some embodiments, the method comprises identifying a subject having an indication (e.g, disease or disorder) as disclosed herein, and administering the Gal-1/Gal-3 dimer and/or monomer(s).

Kits Containing the Gal-1/Gal-3 Dimer and/or Monomer(s) and Pharmaceutical Formulations Thereof The Gal-1/Gal-3 dimer and/or monomer(s) and pharma-ceutical formulations thereof described herein can be pre-sented as a combination kit. As used herein, the terms "combination kit" or "kit of parts" refers to the Gal-1/Gal-3 dimer and/or monomer(s) and pharmaceutical formulations thereof and any additional components that are used to package, sell, market, deliver, and/or administer the combi-nation of elements or a single element, such as the active ingredient, contained therein. Such additional components include but are not limited to, packaging, syringes, blister packages, bottles, and the like. When one or more of the components (e.g., active agents) contained in the kit are administered simultaneously, the combination kit can con-tain the active agents in a single pharmaceutical formulation (e.g., a tablet) or in separate pharmaceutical formulations.

The combination kit can contain each agent, compound, pharmaceutical formulation or component thereof described herein, in separate compositions or pharmaceutical formu-lations. The separate compositions or pharmaceutical for-mulations can be contained in a single package or in separate packages within the kit. Also provided in some embodi-ments, are buffers, diluents, solubilization reagents, cell culture media and other reagents. These additional compo-nents can be contained in a single package or in separate packages within the kit.

In some embodiments, the combination kit also includes instructions printed on or otherwise contained in a tangible medium of expression. The instructions can provide infor-mation regarding the content of the t Gal-1/Gal-3 dimer and/or monomer(s) and pharmaceutical formulations thereof and/or other auxiliary and/or secondary agent contained therein, safety information regarding the content of the Gal-1/Gal-3 dimer and/or monomer(s) and pharmaceutical formulations thereof and/or other auxiliary and/or secondary agent contained therein, information regarding the dosages, indications for use, and/or recommended treatment regimen(s) for the Gal-1/Gal-3 dimer and/or monomer(s) and pharmaceutical formulations thereof and/or other aux-iliary and/or secondary agent contained therein. In some embodiments, the instructions can provide directions for administering the Gal-1/Gal-3 dimer and/or monomer(s) and pharmaceutical formulations thereof and/or other auxiliary and/or secondary agent to a subject having a protein defi-ciency (e.g., a Gal-1 and/or Gal-3 deficiency), periodontal disease, an autoimmune disease, inflammation, inflamma-tory disease and/or a symptom thereof. In some embodi-ments, the subject in need thereof can have arthritis. In some aspects, the arthritis is osteoarthritis. In some embodiments, the arthritis is rheumatoid arthritis. In some embodiments, the subject can have type 1 diabetes. In some embodiments, the subject can have multiple sclerosis. In some embodi-ments, the subject can have graft versus host disease. In some embodiments, the subject can have colitis. In some embodiments, the subject can have uveitis. In some embodi-ments, the subject can have transplant rejection.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understand-ing of the principles of the disclosure. Many variations and modifications may be made to the disclosed embodiment(s) of the disclosure without departing substantially from the spirit and principles of the disclosure. All such modifications and variations are within the scope of this disclosure.

EXAMPLES

Now having described the embodiments of the present disclosure, in general, the following Examples describe some additional embodiments of the present disclosure. While embodiments of the present disclosure are described in connection with the following examples and the corre-sponding text and figures, there is no intent to limit embodi-ments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, tempera-ture, etc.), but some errors and deviations should be accounted for. Unless indicated otherwise, parts are parts by weight, temperature is in Celsius (° C.), and pressure is at or near atmospheric. Standard temperature and pressure are defined as 20° C. and 1 atmosphere (atm).

Example 1: G1/G3 Fusion Proteins

Introduction

Although glycobiology research was first recognized in the early 19th century, researchers are just now beginning to understand the complex role of lectins and glycans within the immune system.[1,2] Galectins are a family of soluble, beta-galactoside-binding lectins that regulate the phenotype and function of various immune cells during the initiation and resolution of immune responses.[3] For example, galec-tin-1 (G1) and galectin-3 (G3) are mediators of tumor immunosuppression and fetal-maternal tolerance, regulate autoimmune disease progression, can enhance or inhibit viral infection, and induce pro-inflammatory responses during osteoarthritis.[4-10]

Extracellular G1 and G3 can act on innate immune cells, including monocytes, macrophages, neutrophils, and dendritic cells, yet it is their influence on T cells that receives the most attention for immunotherapy.[11-18] Extracellular G1 and G3 can induce T cell apoptosis, regulate antigen-specific T cell activation, and alter T cell cytokine secretion.[19] Despite sharing binding affinity for beta-galactoside glycans, though, G1 and G3 often evoke these changes in T cells by recognizing different cell surface glycoproteins, suggesting they function through different signalling pathways.[19,20] For example, although both G1 and G3 bind to CD45, only G1 induces CD45 clustering to trigger T cell apoptosis.[21] Both G1 and G3 have been shown to interact with CD7, yet G3 binding to CD7 does not trigger T cell death.[22-24] G1 can bind to CD2 and CD3, whereas G3 binding to these glycoproteins has not been observed.[22,24] G1 can also selectively induce death of T helper (Th)1 and Th17 cells, yet has no effect on Th2 and regulatory T cells, due to polarization-induced changes in the T cell surface glycosylation profile.[25] Similarly, G3 preferentially kills double-negative thymocytes, but not double-positive thymocytes, again due to alterations in the surface glycosylation profile of cells as they mature or polarize.[22] Interestingly, a combination of G1 and G3 did not have an additive or synergistic effect on T cell apoptosis, but rather elicited a similar extent of cell death as either galectin alone, possibly due to competitive interactions with CD45 or other T cell surface glycoproteins.[22] Beyond apoptosis, G1 has been shown to stimulate antigen-specific T cell responses while G3 antagonized these responses, yet in other contexts both G1 and G3 can regulate T cell receptor clustering and signaling.[26] Finally, G1 and G3 also have differing effects on T cell cytokine secretion, with low concentration G3 inducing IL-2 secretion, while G1 upregulates IL-10 expression by Th17 cells.[27,28]

In light of these diverse effects on T cells, exogenous galectins and engineered variants have been evaluated as therapeutics to regulate adaptive immunity in various contexts.[4] Recombinant G1 has received the most attention to date, and has demonstrated efficacy in rodent models of Crohn's disease, multiple sclerosis, myasthenia gravis, rheumatoid arthritis, graft vs host disease, autoimmune uveitis, and T cell mediated hepatitis.[5-8,29-32] A key aspect of G1 and G3 extracellular activity is their non-covalent self-association into quaternary structures with multiple carbohydrate-recognition domains (CRDs). For example, G1 associates into homodimers at relatively high (μM) concentrations.[33] To stabilize its activity in dilute conditions, G1 dimers formed via a polypeptide linker, a synthetic polymer, a leucine zipper coiled-coil forming peptide, or an IgG Fc domain were engineered.[4,34-37] Often, these engineered G1 variants demonstrate a minimum effective dose that is approximately 10-fold lower than that of the wild-type protein. In contrast, G3 is unique among galectins in that it assembles into higher-ordered oligomers (≥2 G3 molecules) upon glycan binding via interactions involving its N-terminal domain.[38] No engineered G3 oligomers with improved activity have been reported. Rather, G3 inhibitors have been developed by treating the wild-type protein with collagenase, which cleaves the N-terminal domain without disrupting the CRD.[39] Likewise, it was recently reported G3 fusion proteins that bind glycans yet lack activity for inducing T cell agglutination, apoptosis, and cytokine secretion because they cannot oligomerize.[40] Together, these examples demonstrate the potential of protein engineering approaches to manipulate G1 and G3 immunomodulatory activity by altering their oligomerization.[41] Despite these efforts, though, existing engineered G1 and G3 variants still have minimum effective doses that are in the low μM range (0.5-5 μM), which is impractical for many therapeutic applications.

As described herein, one way to further decrease the effective dose of G1 and G3 can be to combine them into chimeric multivalent assemblies. In one aspect, a construct was created in which G1 was connected to the N-terminus of G3 via a flexible linker ("G1/G3") (FIG. 1). This design was based on a recent report demonstrating that fusing enzymes to the N-terminus of G3 endowed them with carbohydrate-binding affinity, yet also abolished G3's activity for inducing T cell apoptosis.[40] The G3 domain can primarily serve to anchor G1 at the T cell surface by increasing its affinity for membrane glycans. In some aspects of this example, a construct in which G1 was connected to G3 via a peptide domain derived from GCN4 that forms a two-stranded parallel alpha-helical coiled-coil ("G1/G3 dimer") (FIG. 1) was generated.[42] The design was such that this construct design would be expected yield a variant with a lower effective dose by stabilizing the active homodimeric structure of G1, yet would not restore G3 signalling activity based on a prior report demonstrating that a trimeric G3 assembly does not induce T cell apoptosis.[40] In all designs, a variant of G1 which has all four surface cysteine residues mutated to serine residues (C2S, C16S, C88S, C130S) was employed to avoid oxidative inactivation.[37,43-45] Lactose binding affinity, solution-phase glycoprotein crosslinking, and extracellular activity of G1, G1/G3, G1/G3 dimer, and a recently reported G1 dimer formed by reacting a single surface cysteine with poly(ethylene glycol) diacrylate ("G1-PEG-G1").[37] The results can demonstrate that G1/G3 was inactive as an extracellular signal, whereas G1/G3 dimer had higher carbohydrate-binding affinity and a significantly lower minimum effective dose than G1 or G1-PEG-G1 for inducing Jurkat T cell apoptosis in vitro.

Results and Discussion

Design, Expression, and Characterization of G1/G3 Variants

Figure 8:
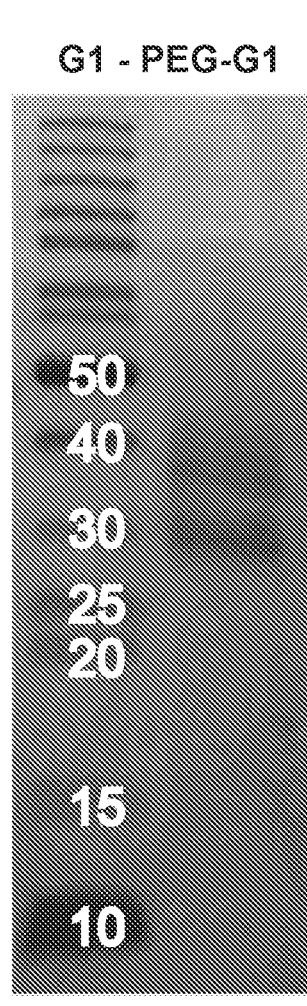
FIG. 8 can show a representative image of a SDS-PGE gel that demonstrate synthesis of G1-PEG-G1. To synthesize a stable homodimeric G1 variant ("G1-PEG-G1") a previously reported protocol was used.[1] In particular, 30 $\mu$M of a G1 variant having one cysteine residue on its surface ("C2S/C16S/C88S G1") was stirred with 25-fold excess of poly (ethylene glycol) diacrylate (Mn=2000 Da) overnight protected from light at room temperature. The resulting product was characterized with SDS-PAGE.
Figure 9:
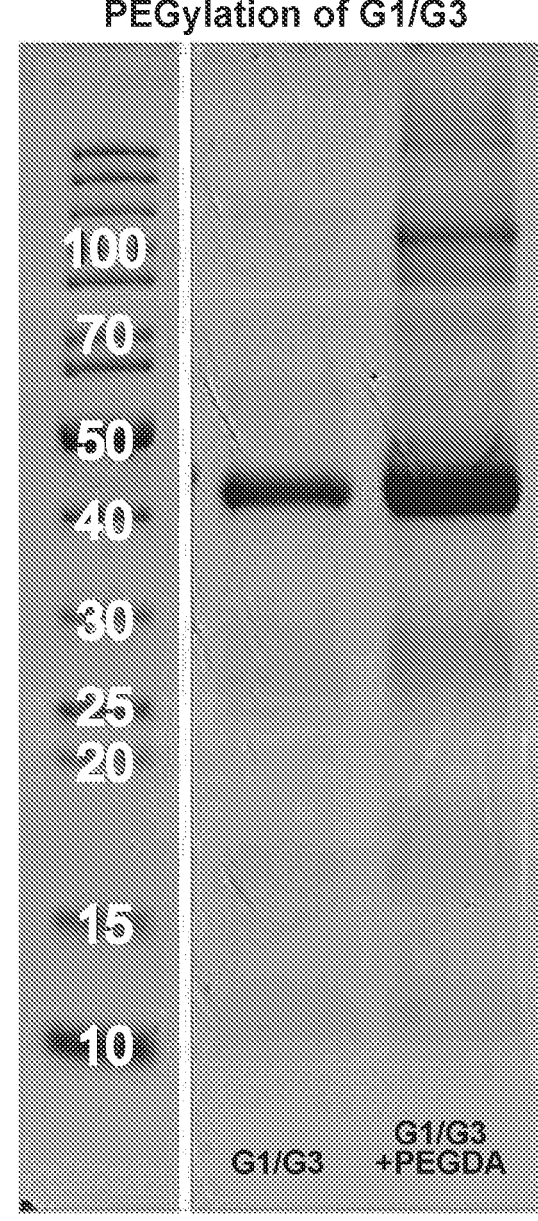
FIG. 9 shows a representative image of a SDS-PGE gel that can demonstrate PEGylation of G1/G3. A G1/G3 variant with one surface cysteine ("(C2S/C16S/C88S)G1/G3") was expressed and purified using similar methods as reported for G1/G3. Formation of a G1/G3 dimer via PEGylation ("G1/G3-PEG-G1/G3") was attempted by adapting the previously reported protocol for synthesis of G1-PEG-G1.1. The resulting product was characterized with SDS-PAGE. The product of the G1/G3+PEGDA reaction migrated to a similar distance as G1/G3 in the absence of PEGDA demonstrating that G1/G3-PEG-G1/G3 was not formed.

All Galectin-1 (G1) mutants and fusions were expressed in *E. coli* and recovered from the soluble fraction in >90% purity and mg/L yields (FIG. 2A). G1/G3, G1/G3 dimer, and G1 migrated to distances corresponding to their predicted molecular weights under denaturing gel electrophoresis conditions. The slightly shorter migration distance for G1/G3 dimer relative to G1/G3 was expected due to its higher denatured molecular weight which is attributed to the addition of the coiled-coil domain (FIG. 2A). G1-PEG-G1 was prepared as previously reported (FIG. 8).[37] Preparation of a PEG-crosslinked G1/G3 dimer was also attempted, and while it was generated the amount produced was below a workable amount (FIG. 9). Size-exclusion chromatography (SEC) demonstrated that the hydrodynamic size of G1/G3 dimer was larger than that of G1/G3 under native conditions (FIG. 2B). The hydrodynamic sizes of G1/G3 dimer and G1/G3, which were estimated by fitting their SEC elution volumes to a standard curve, were consistent with their predicted native molecular weights (FIG. 2B table). Further, G1/G3 dimer had a larger hydrodynamic diameter than G1/G3 via dynamic light scattering number-weighted size distribution (FIG. 2C). These observations can demonstrate that G1/G3 fusions can be expressed and purified in high yield and purity, and that a peptide that forms a two-stranded α-helical coiled-coil can be used to assemble a G1/G3 dimer.

Figures 3A, 3B, 3C:
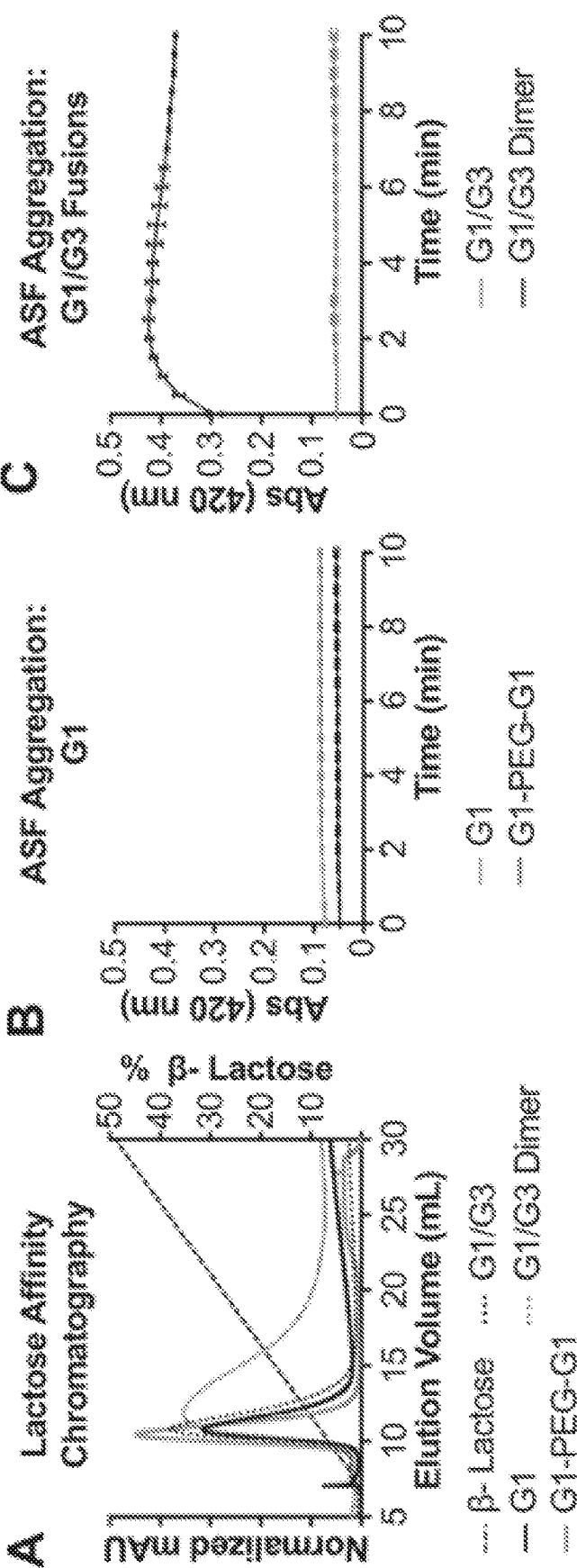
FIGS. 3A-3C show results that demonstrate carbohydrate binding and glycoprotein crosslinking properties of G1 variants and G1/G3 fusions.
Figure 10:
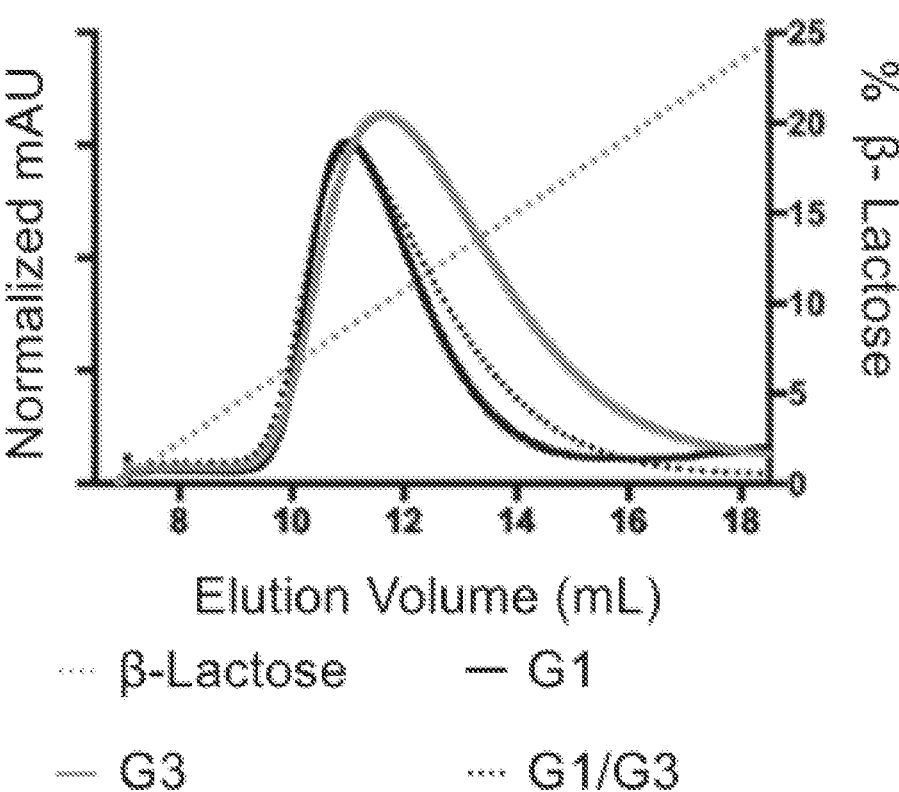
FIG. 10 shows results from lactose affinity chromatography of G1, G3, and G1/G3. Proteins were eluted with a linear gradient of β-lactose in PBS. Proteins were detected via absorbance at 280 nm. The right shifted elution volume for G3 indicated it had higher affinity for immobilized lactose than G1 or G1/G3.

Carbohydrate Binding and Glycoprotein Crosslinking Properties of G1/G3 Fusion Proteins The carbohydrate-binding properties of G1/G3 and G1/G3 dimer was compared to G1 and G1-PEG-G1 using lactose affinity chromatography. G1, G1-PEG-G1, and G1/G3 eluted at similar concentrations of soluble lactose, whereas G1/G3 dimer eluted at a higher soluble lactose concentration with a broader distribution profile (FIG. 3A). Collectively, these observations suggested that engineering G1 to have 2 CRDs did not establish avidity effects that significantly increased its apparent binding affinity for immobilized lactose, regardless of whether G1 was linked to another G1 molecule or to G3. Unexpectedly, these data also suggested that the G1 CRD of G1/G3 may preferentially interact with immobilized lactose, given that it was observed that G3 has higher affinity for immobilized lactose than G1 (FIG. 10). In contrast and unexpectedly, G1/G3 dimer had higher apparent binding affinity for immobilized lactose than G1, G1-PEG-G1, or G1/G3, suggesting that assembly of G1 and G3 into a structure having 4 CRDs established multivalent avidity effects not afforded by only having 2 CRDs.

Galectins can crosslink soluble glycoproteins into microscopic aggregates via their multiple CRDs[46-48], and galectin-mediated crosslinking of cell surface glycoconjugates has been proposed as the mechanism by which galectins regulate outside-in signaling.[49-52] Turbidity as a model was used to characterize crosslinking of the soluble glycoprotein, asialofetuin (ASF), via G1, G1-PEG-G1, G1/G3, or G1/G3 dimer. At the concentration tested, neither G1, G1-PEG-G1, nor G1/G3 crosslinked ASF into insoluble aggregates (FIGS. 3B-3C). In contrast, G1/G3 dimer rapidly crosslinked ASF into aggregates, as demonstrated by a significant increase in solution turbidity (FIG. 3C). In previous reports, G1 was able to crosslink ASF at higher concentrations than those used here.[53] Likewise, previous reports demonstrated that wild-type G3 can also crosslink ASF into aggregates; however, it was previously reported that G3 lost its ability to crosslink ASF when a non-galectin protein was fused to its N-terminus.[40] Taken together, these data demonstrated that G1 variants having CRD valency <2 (i.e., G1, G1/G3, and G1-PEG-G1) cannot crosslink ASF at the conditions tested, whereas G1/G3 dimer having a CRD valency of 4 can. A previous study reported that G1 and G3 have comparable affinity for ASF, and in all experiments the total G1 and G3 CRD concentration was maintained constant, which suggested that the lower threshold for crosslinking soluble glycoproteins was not due to an affinity advantage afforded by having G1 versus G3 present. Rather, these observations suggested that assembling G1 and G3 into structures having higher CRD valency decreased the threshold for glycoprotein crosslinking by establishing avidity effects that favored protein-glycan interactions, such as statistical rebinding. Based on these observations, it was reasoned that G1/G3 dimer would have a lower effective dose as an extracellular signal when compared to G1, G1/G3, or G1-PEG-G1.

Extracellular Activity of G1/G3 Fusion Proteins

Figure 4A:
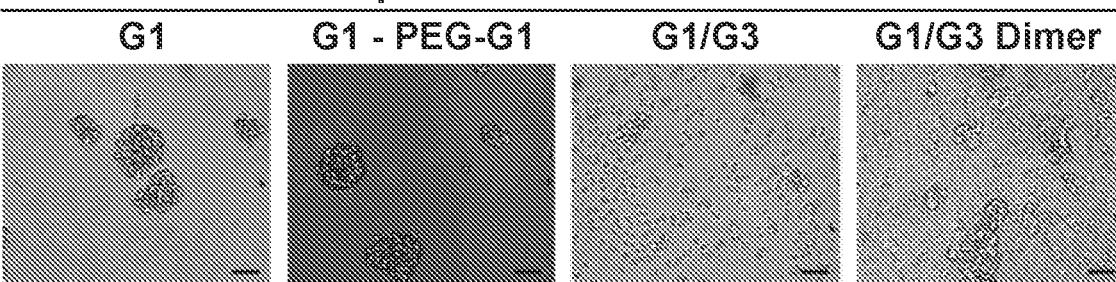
FIGS. 4A-4C show results that demonstrate Jurkat T cell agglutination and metabolic activity. Brightfield micrographs of Jurkat T cells after 18 hours treatment with (FIG. 4A) 5 micrometers ($\mu$M) or (FIG. 4B) 0.5 $\mu$M G1, G1-PEG-G1, G1/G3, or G1/G dimer.
Figure 4B:
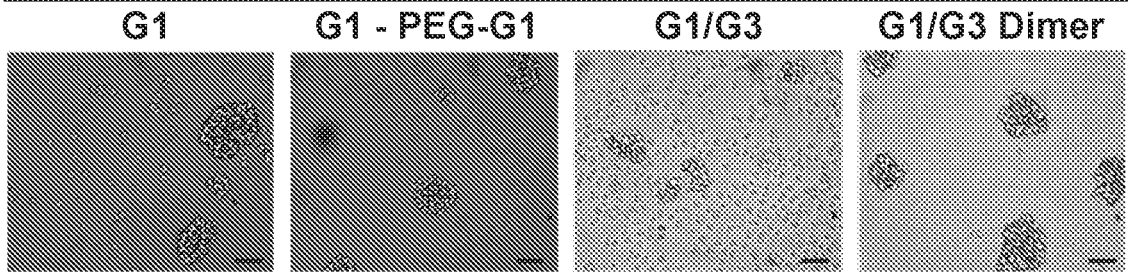
Figure 11A:
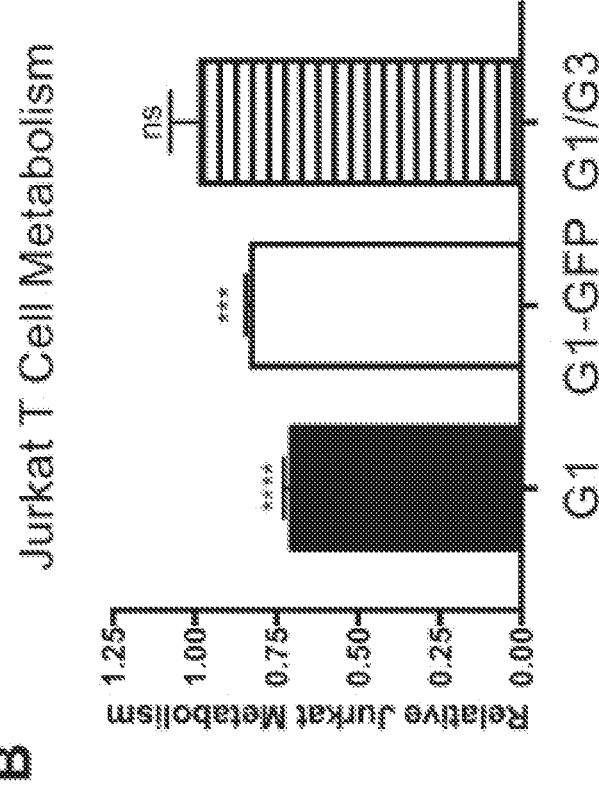
FIGS. 11A-11B show results that demonstrate G1-GFO agglutination and Jurkat metabolism, specifically G1-GFP bioactivity on Jurkat T cells.
Figure 11B:
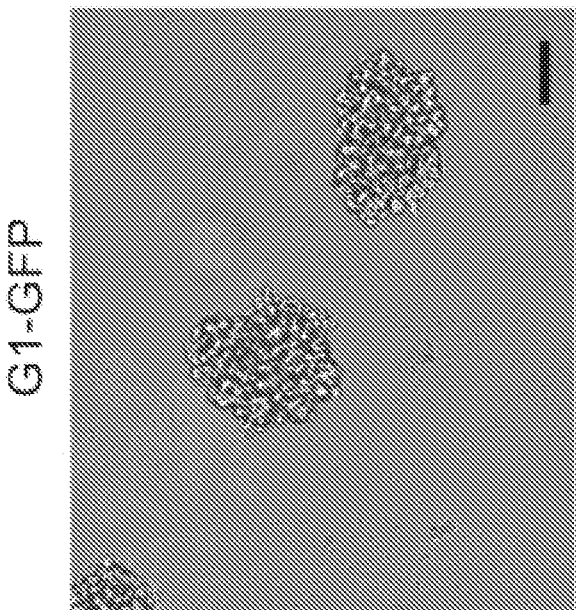

The relative activity of G1, G1-PEG-G1, G1/G3, and G1/G3 dimer to induce Jurkat T cell agglutination and apoptosis. After 18 hours, high concentration G1 and G1-PEG-G1 induced Jurkat T cell agglutination, consistent with prior reports (FIG. 4A).[37] Interestingly, G1/G3 did not agglutinate Jurkat T cells after 18 hours, while high concentration G1/G3 dimer did; however, many undefined micron-sized particulates were also visible in the culture media of samples treated with G1/G3 dimer, which were not present in cells treated with G1, G1-PEG-G1, or G1/G3. To understand the dose dependence of agglutination, cells were treated with a lower concentration of G1, G1-PEG-G1, G1/G3, and G1/G3 dimer ([G1]=0.5 µM) (FIG. 4B). Few cells were agglutinated in the presence of 0.5 µM G1, while low concentration G1-PEG-G1 induced significant cell agglutination, consistent with a prior report.[37] Low concentration G1/G3 did not induce agglutination, which was not surprising since this protein also failed to induce agglutination at a 10-fold higher concentration. Some cell aggregates were observed in cultures treated with low concentration G1/G3 dimer, although single cells were also observed. Notably, much fewer micron-sized particulates were observed in cultures treated with low concentration G1/G3 dimer when compared to high concentration G1/G3 dimer cultures, suggesting that this effect was concentration dependent. FIGS. 11A-11B show G1-GFP agglutination and Jurkat metabolism.

Figure 4C:
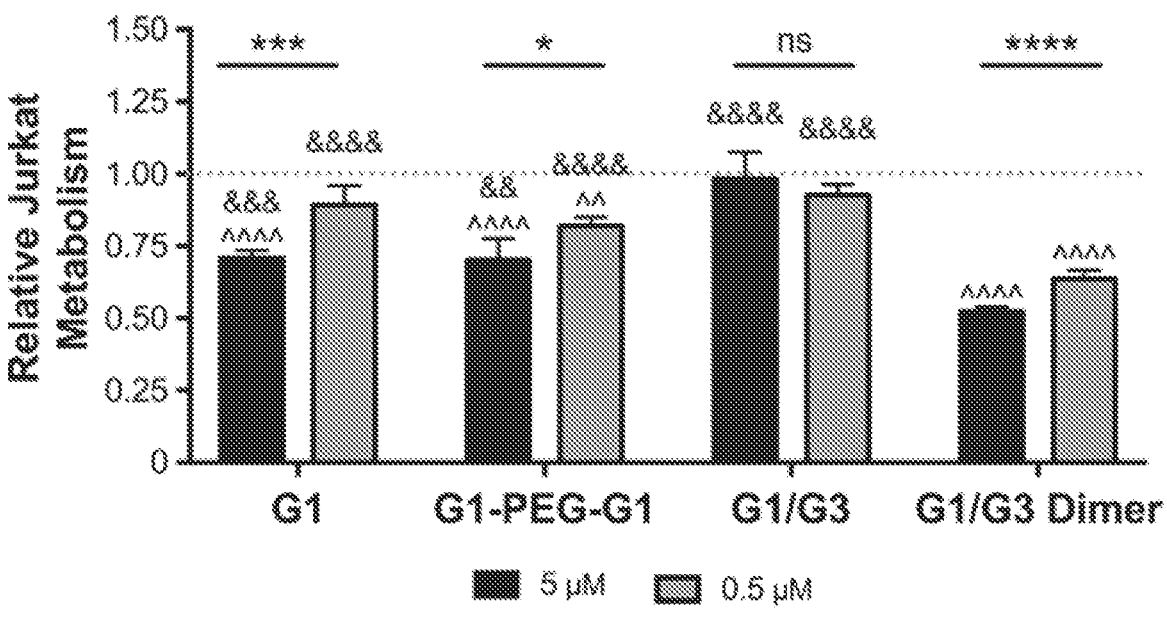
Figure 5A:
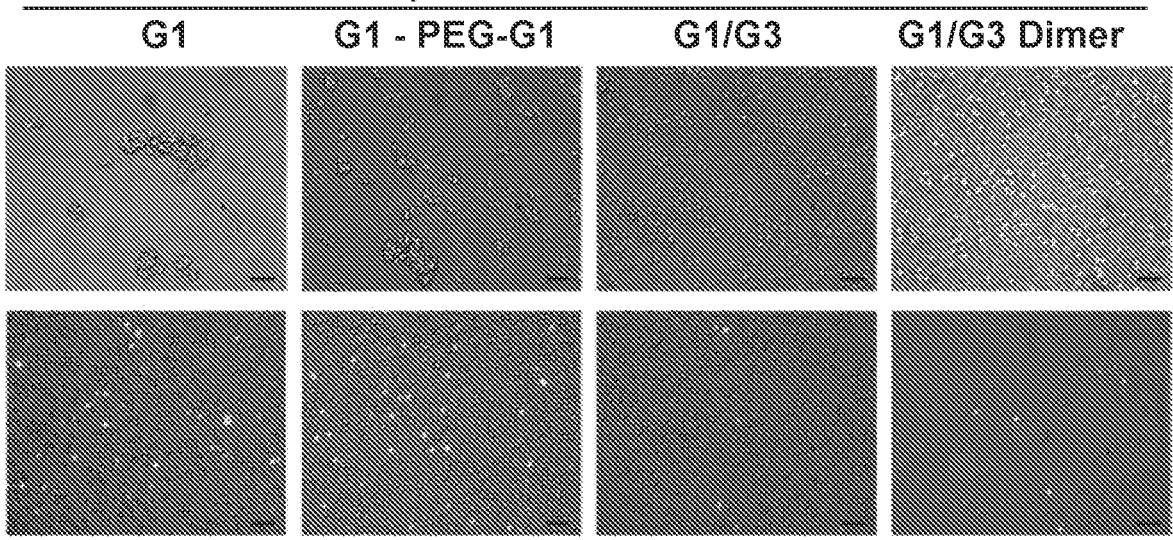
FIGS. 5A-5B show results of phosphatidylserine exposure as determined via Annexin VFITC staining (green) and membrane permeability determined via propidium iodide (PI) (red) after Jurkat T cells were treated with (FIG. 5A) 5 $\mu$M or (FIG. 5B) 0.5 $\mu$M G1, G1-PEG-G1, G1/G3, or G1/G3 dimer for 4 h. Brightfield images in top row are representative of extent of agglutination before treatment with b-lactose. Single channel fluorescence images are available in FIG. 12. Scale bars=50 $\mu$M.
Figure 5B:
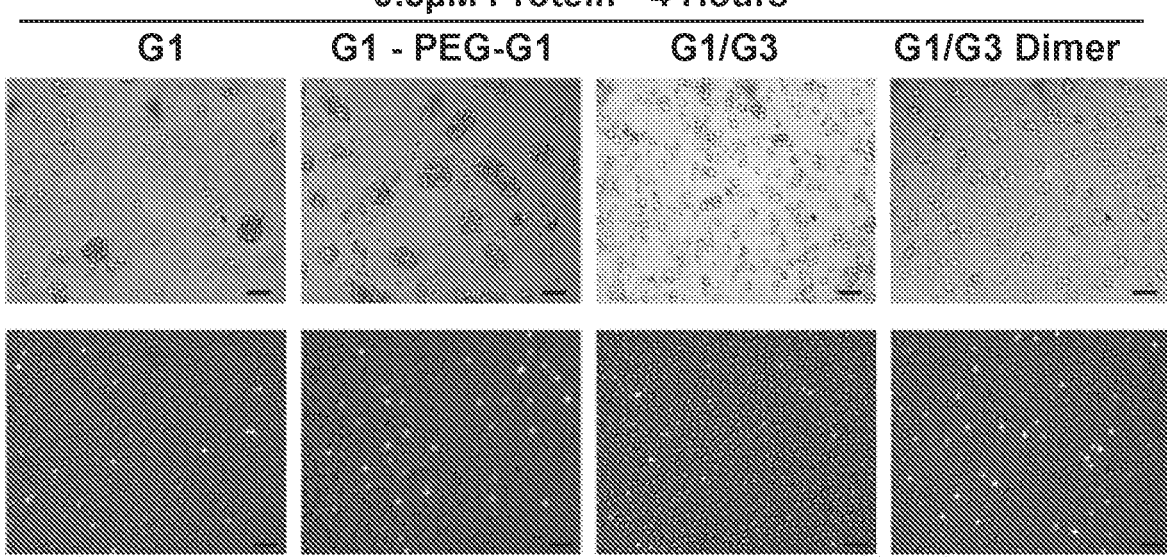
Figure 12:
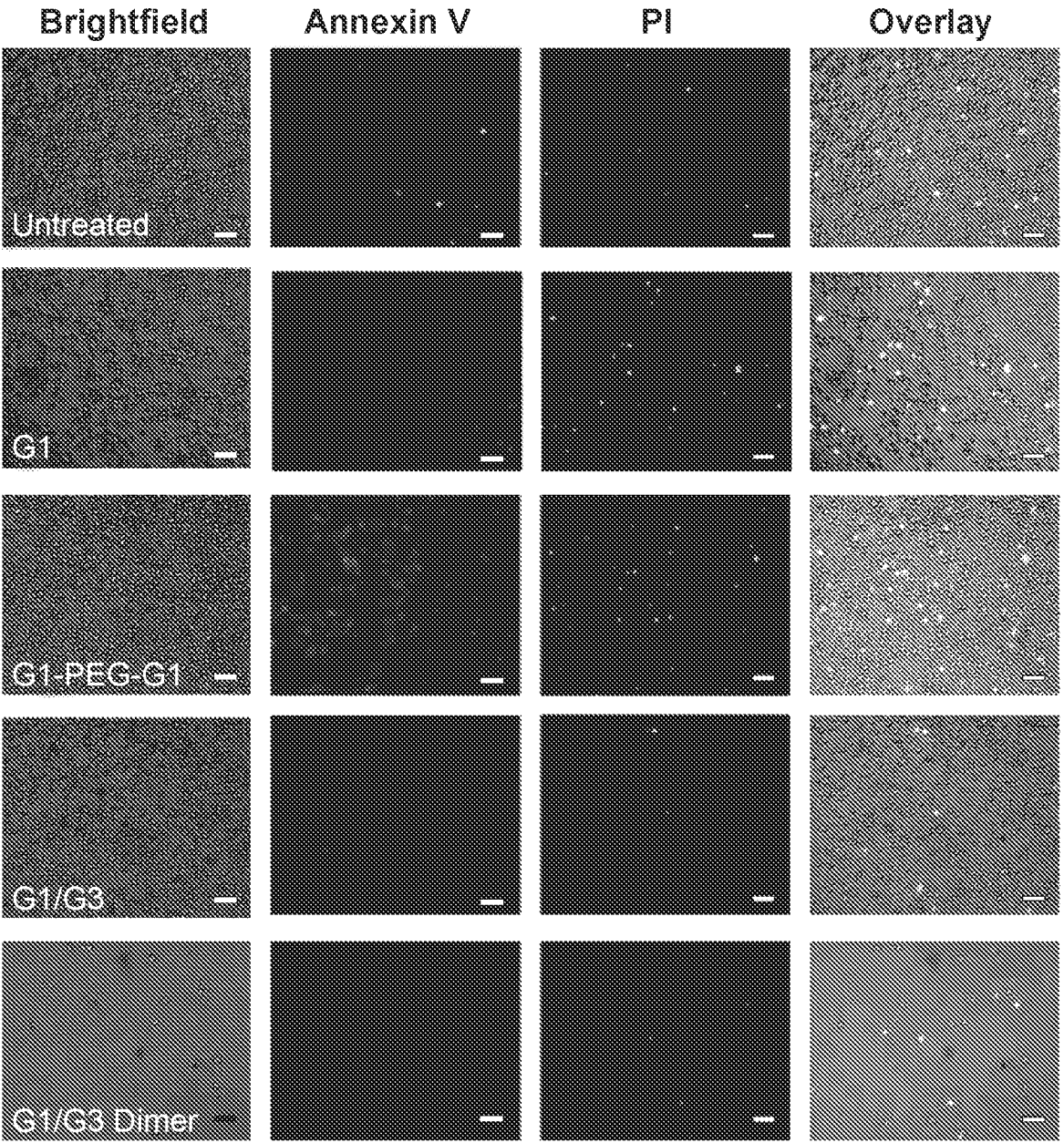
FIG. 12 shows results that demonstrate Annexin V and PI staining of protein treated Jurkat T Cells. Phosphatidylserine exposure was determined via Annexin V-FITC staining and membrane permeability was determined via propidium iodide (PI) after Jurkat T cells were treated with 5 μM protein for 4 hours. Scale bars are 50 μM.

In addition to inducing agglutination, G1 and G3 can also alter T cell metabolism. Here, changes in Jurkat T cell NADH content mediated by G1, G1-PEG-G1, G1/G3, or G1/G3 dimer using the CellTiter-Blue® assay were compared (FIG. 4C). G1 only decreased Jurkat T cell metabolism at a high concentration, whereas G1-PEG-G1 decreased Jurkat T cell metabolic activity at both high and low concentration, consistent with prior reports.[33,37] G1/G3 failed to alter Jurkat T cell metabolic activity at any concentration tested, whereas G1/G3 dimer decreased Jurkat T cell metabolic activity at both high and low concentrations to a significantly greater extent than G1 or G1-PEG-G1. Taken together with agglutination data, these observations suggested that G1/G3 generally lacks activity for inducing T cell death. This loss of activity could be due to many factors, such as perturbation of G1 homodimerization when fused to G3; however, G1 fused to GFP induced Jurkat T cell phosphatidylserine exposure and membrane permeability, two markers typically associated with early and late apoptosis, respectively (FIGS. 5A-5B and 12). Because galectins induce changes in these markers within a few hours, here the outer leaflet phosphatidylserine was visualized via Annexin V staining and membrane permeability via propidium iodide (PI) staining 4 hours after treatment with high or low concentration G1, G1-PEG-G1, G1/G3, or G1/G3 dimer.[54,55] In most instances, extent of cell agglutination after 4 hours was consistent with observations made at 18 hours (FIGS. 4A-4B), with the exception of cells treated with low concentration of G1/G3 dimer, which were not appreciably agglutinated (FIG. 5B). Prior to Annexin V and PI staining, all agglutinated cell aggregates were dissociated with β-lactose. G1-PEG-G1 induced Jurkat T cell phosphatidylserine exposure and increased PI permeability at high and low concentrations, whereas G1 only induced these changes at high concentration, consistent with the loss of G1 activity at concentrations below the monomer-dimer dissociation constant. G1/G3 did not induce significant phosphatidylserine exposure or PI permeability at any concentration tested, again suggesting this fusion lacked the extracellular activity of G1 and G3. In contrast and unexpectedly, G1/G3 dimer induced PI permeability in a high percentage of cells at low and high concentration; however, the total number of cells recovered from samples treated with high concentration G1/G3 dimer was significantly lower than that recovered from cultures treated with high concentration G1, G1-PEG-G1, or G1/G3. These observations suggested that many cells treated with high concentration G1/G3 dimer may already be in a very late stage of apoptosis by 4 hours, and that some of the micron-sized particulates observed in the culture may be apoptotic bodies or fragmented cells that were not recovered via centrifugation. Interestingly, the induction of phosphatidylserine exposure and PI permeability by low concentration G1/G3 dimer in the absence of agglutination suggests that these processes may not be causally linked in Jurkat T cell response to extracellular G1 and G3. Rather, an engineered G1 variant with high glycan-binding affinity may preferentially crosslink glycoproteins on the cell surface leading to activation of pro-apoptotic signalling pathways instead of mediating the cell-cell interactions that lead to agglutination.

Figures 6A, 6B, 6C, 6D:
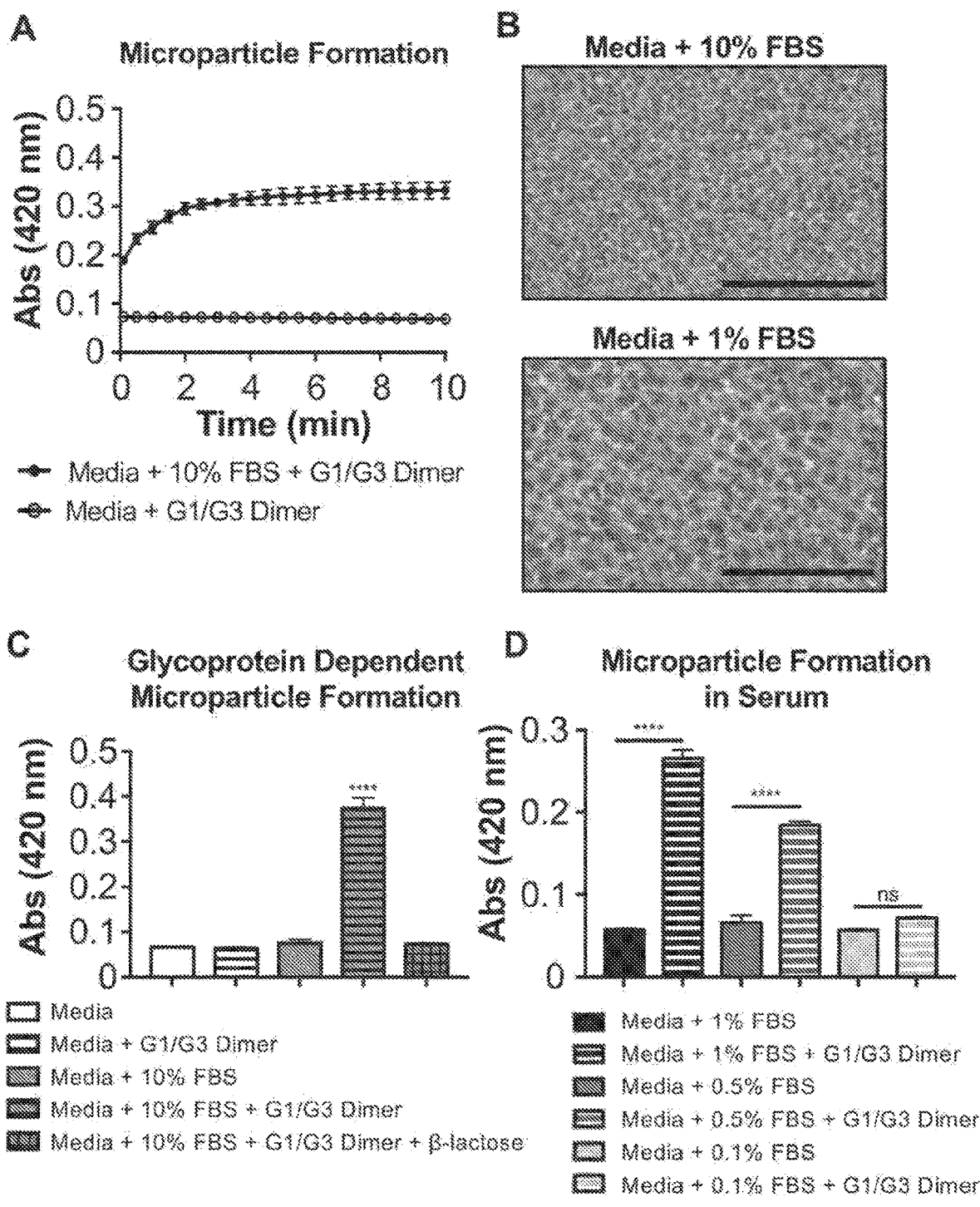
FIGS. 6A-6D show results that demonstrate micron-sized particulates formed via G1/G3 dimer in serum-containing culture media.

Formation of Micron-Sized Particulates Via G1/G3 Dimer in Serum-Containing Culture Media After 4 and 18 hours treatment of Jurkat T cells with high concentration of G1/G3 dimer, micron-sized particulates were observed in the culture media that were largely absent when cells were treated with other proteins. It was previously reported that a trimeric assembly of G3 can form micron-sized particulates in cell cultures by crosslinking G3-binding serum glycoproteins.[40] Here, serum glycoprotein crosslinking was characterized via G1/G3 dimer in the absence of cells using bright-field microscopy and turbidity. No change in turbidity was observed for solutions containing G1/G3 dimer alone, whereas turbidity of solutions containing G1/G3 dimer and 10% fetal bovine serum increased rapidly (FIG. 6A), similar to solutions containing G1/G3 dimer and ASF (FIG. 3C). When visualized with bright-field microscopy, solutions of G1/G3 dimer in media supplemented with serum contained micron-sized particulates similar to those observed in Jurkat T cell cultures (FIG. 6B).

To determine if these particulates formed due to specific interactions between G1/G3 dimer and serum glycoproteins, turbidity of samples was compared with and without β-lactose, a known inhibitor of G1 and G3 glycan binding. Solutions of containing 10% serum and G1/G3 dimer were significantly more turbid than solutions of serum-free media, serum-free media plus G1/G3 dimer, or serum-containing media alone (FIG. 6C). Solutions of serum-containing media plus G1/G3 dimer and β-lactose had low turbidity, which was comparable to solutions without G1/G3 dimer or with 10% FBS alone (FIG. 6C) Likewise, turbidity significantly decreased as the serum concentration was decreased from 10 to 0.5%, with solutions containing 0.1% serum and G1/G3 dimer having comparable turbidity to 0.1% serum alone (FIG. 6D). Together, these observations suggested that at least some of the micron-sized particulates observed in Jurkat T cell cultures treated with G1/G3 dimer may be due to serum glycoprotein crosslinking through specific interactions with G1 or G3 CRDs. Given that G3 binds to a broader assortment of serum glycoproteins with higher affinity than G1,[56] it can be that G3 is the primary mediator of these interactions, although it is plausible that G1 presented in this multivalent configuration may also be involved in serum glycoprotein crosslinking.

G1/G3 Dimer Extracellular Activity in Serum Free Conditions

Figure 7A:
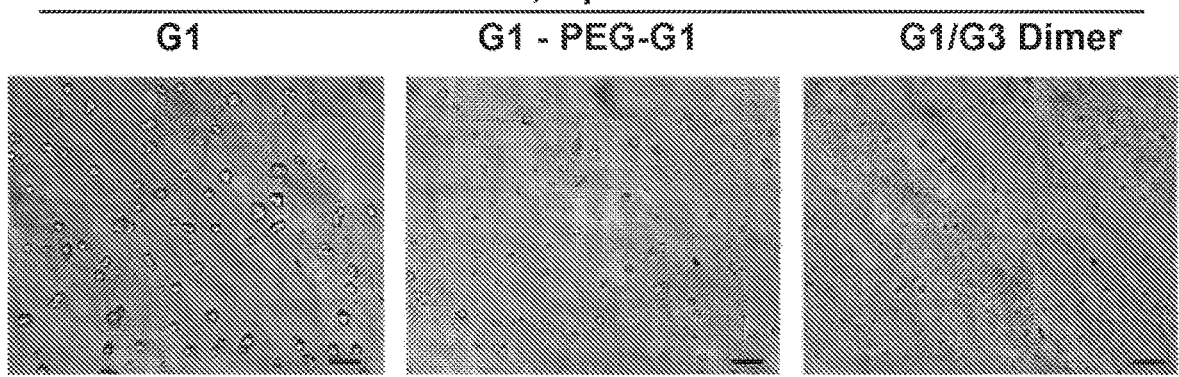
FIGS. 7A-7C show results that demonstrate extracellular activity of G1/G3 dimer in serum-free media. Brightfield micrographs of Jurkat T cells after 18 hours treatment with (FIG. 7A) 5 $\mu$M or (FIG. 7B) 0.5 $\mu$M G1, G1-PEG-G1, or G1/G3 dimer.
Figure 7B:
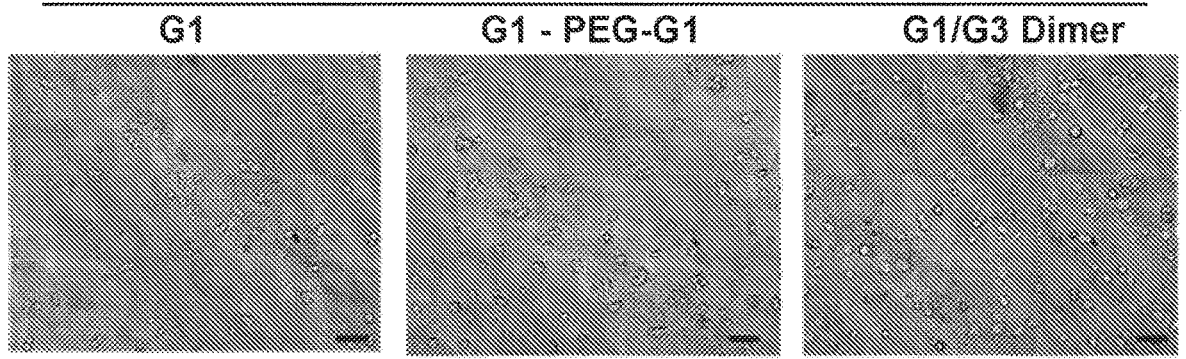
Figure 7C:
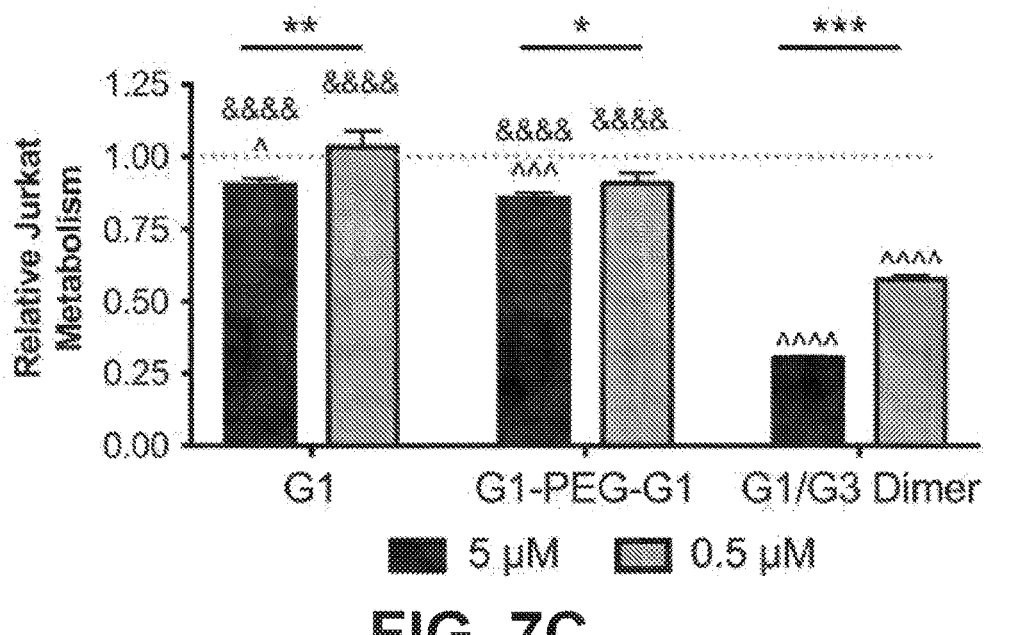

CRD-Dependent interactions with serum glycoproteins could alter the biological activity of the G1/G3 dimer, for example by inhibiting its binding to cell surface glycoproteins, similar to competitive interactions reported previously between G3, serum glycoproteins, and a candidate multivalent G3 inhibitor.[57] Here Jurkat T cell agglutination and metabolic activity during culture was compared in serum-free media supplemented with G1, G1-PEG-G1, and G1/G3 dimer. Neither G1, nor G1-PEG-G1, nor G1/G3 dimer induced significant agglutination of Jurkat T cells at either high or low concentration in serum-free media, strongly suggesting that serum proteins or glycoproteins contribute directly to galectin-mediated T cell agglutination (FIGS. 7A-7B). G1 and G1-PEG-G1 have weakened activity for decreasing metabolic activity of Jurkat T cells cultured in serum-free media when compared to their activity in media supplemented with serum (FIGS. 4C and 7C). Conversely, G1/G3 dimer has increased activity for suppressing metabolic activity of Jurkat T cells cultured in serum-free media when compared to its activity in media supplemented with serum (FIG. 4C and FIG. 7C). Micron-sized particulates were observed in cultures of Jurkat T cells treated with high concentration G1/G3 dimer in serum-free media, which are likely cell fragments or apoptotic bodies. Thus, the micron-sized particulates observed in serum-supplemented cultures of Jurkat T cells treated with G1/G3 dimer are likely a mixture of both cell fragments and crosslinked serum glycoproteins. Taken together, these data can suggest that specific interactions with serum glycoproteins can diminish the extracellular activity of G1/G3 dimer by sequestering it within micron-sized particulates that cannot bind to cell surface glycans as effectively as free protein.

Conclusions

This work demonstrates a chimeric, multivalent assembly of G1 and G3 with improved extracellular activity when compared to G1, G1-PEG-G1, or a monomeric G1/G3 fusion protein. G1/G3 dimer has higher apparent binding affinity for lactose, as shown via immobilized lactose affinity chromatography, and crosslinked glycoproteins at a lower concentration than G1, G1-PEG-G1, or a G1/G3 fusion protein, as shown with ASF turbidity measurements. G1/G3 dimer decreased T cell metabolism at both high and low concentrations to a greater extent than G1 and G1-PEG-G1, and was the only galectin variant that was effective at inducing T cell death at low concentrations under serum-free conditions. In contrast, G1/G3 failed to induce T cell death in any condition tested. G1/G3 may be inactive because G1 and G3 mediate T cell apoptosis via binding to different cell surface glycoproteins and reconfiguring these interactions by fusing G1 to G3 may preclude receptor clustering or lattice formation that are necessary to activate pro-apoptotic signalling pathways or induce changes in cell metabolism. The CellTiter-Blue® assay used here to determine metabolic activity indirectly measures NADH concentration via NADH-dependent reduction of resazurin to resorufin by mitochondrial enzymes.[58] Thus, these observations can suggest that G1/G3 dimer may more effectively suppress NADH-dependent metabolic processes related to T cell viability, activation, and division, such as the citric acid cycle, ATP generation, and nucleotide synthesis, although future research will be needed to identify the specific metabolic pathways that are perturbed. Interestingly, G1/G3 dimer did not cause Jurkat T cell agglutination at 4 h, a trait commonly associated with galectin-like activity, yet did induce changes in markers associated with apoptosis, suggesting that these processes may not be operatively linked in Jurkat T cell response to extracellular galectins. Rather, assembling G1 and G3 into a multimeric configuration can result in a lower effective dose because CRD domains are preferentially involved in crosslinking cell surface glycoproteins (i.e., intra-cellular interactions) and, in turn, activating pro-apoptotic signalling cascades rather than mediating cell-cell adhesion (i.e., inter-cellular interactions). This work can support that a G1/G3 dimer could be used as an immunotherapeutic, where coupling G1 dimerization with the use of G3 as an anchoring domain could yield lower effective doses and may also extend local half-life as seen previously with enzymes fused to G3.[40]

Materials and Method

Protein Expression and Purification

Origami B (DE3) *E. coli* (Novagen) were transformed with pET-21d-C2S/C16S/C88S/C130S Galectin1, pET-21d-C2S/C16S/C88S/C130S Galectin1-Galectin3, and pET-21d-C2S/C16S/C88S/C130S Galectin1-Galectin3 Dimer vectors and selected on 100 μg/mL ampicillin- and 50 μg/mL kanamycin A-doped LB/agar plates overnight at 37° C. Positive clones were selected to inoculate 5 mL 100 μg/mL ampicillin- and 50 μg/mL kanamycin A-containing LB broth. Cultures were grown overnight at 37° C., 220 rpm on an orbital shaker. Cultures of positive clones were then subcultured into 1 L 100 μg/mL ampicillin- and 50 μg/mL kanamycin A-containing 2×TY broth (10 g/L Yeast, 16 g/L Tryptone, and 5 g/L NaCl) and grown at 37° C., 225 rpm on an orbital shaker until an optical density of 0.6-0.8 ($\lambda$=600 nm) was reached. Protein expression was induced with 0.5 mM isopropyl β-d-1-thiogalactopyranoside (IPTG) and incubated for 18 hours at 18° C., 225 rpm in an orbital shaker. Bacteria were pelleted by centrifugation, and washed with phosphate buffered saline (PBS). Bacteria were lysed with B-PER (Thermo Fisher), a protease inhibitor tablet (Thermo Fisher), 300 units DNase I from bovine pancreas (Sigma), and 100 μg lysozyme (Sigma) for 20 min. Lysed bacteria was cleared by centrifugation, and supernatant containing recombinant proteins was loaded onto columns containing HisPur™ Cobalt Resin (Thermo Fisher) equilibrated with PBS. Columns were washed with 20-30 column volumes of PBS and bound galectin was eluted with a gradient of imidazole in PBS. Imidazole was removed by centrifugation using Amicon filter tubes (MWCO 10 kDa) (Millipore). Protein molecular weight and purity were analyzed with SDS-PAGE. Protein concentrations were determined using the 660 nm assay (Thermo Fisher) calibrated with bovine serum albumin. Proteins were endotoxin removed using Detoxi-Gel Endotoxin Removing Columns (ThermoFisher) and final endotoxin content was determine using Pierce LAL Chromogenic Endotoxin Quantitation kit (ThermoFisher), according the manufacturer's instructions.

Characterization of Fusion Protein Size and Molecular Weight

Size-exclusion chromatography (SEC) was used to determine fusion protein molecular weight under native conditions. A SuperDex-200 10/30 GL column (GE Healthcare) connected to an ÄKTA pure FPLC system was used. Eluted proteins were detected at A280 nm, which was normalized based on maximum signal intensity. Protein molecular weight was calculated by fitting protein elution volume to a curve prepared using protein standard markers (Bio-Rad, GE Healthcare). Hydrodynamic diameter of fusion proteins was approximated via DLS on a NanoBrook 90Plus Particle Size Analyzer using BIC Particle Sizing Software (Brookhaven Instruments). Hydrodynamic diameter±standard deviation by number-, volume-, and intensity-weighted size distribution was determined from ten 30 s runs in triplicate or more.

Lactose Affinity Chromatography

Lactose binding affinity of G1, G1-PEG-G1, G1/G3, and G1/G3 dimer was determined using affinity chromatography on an AKTA Pure chromatography system (GE Life Sciences) equipped with an α-lactose:agarose column (Sigma-Aldrich). Proteins were eluted with a linear gradient of β-lactose (Sigma-Aldrich) in PBS. Proteins were detected via absorbance at 280 nm. Binding affinity experiments were repeated in triplicate and representative traces were plotted.

Turbidity

Turbidity was measured using absorbance at 420 nm, similar to previously reported methods.[40] 50 μL of 7 μM ASF and 50 μL of 10 μM protein was pipetted into a 96 well plate. Immediately after pipetting the ASF and protein samples, kinetics reads over 10 minutes at 30 second intervals were collected.

Annexin V and Propidium Iodide Staining of Jurkat T Cells

Extracellular activity of G1, G1-PEG-G1, G1/G3 and G1/G3 dimer was characterized using Jurkat T cells, similar to previously reported methods.[37,40,44] For all experiments, cells were first expanded in complete Jurkat T cell media (RPMI 1640 supplemented with 10% heat-inactivated fetal bovine serum, 1% penicillin-streptomycin, L-glutamine 200 mM, 1% HEPES buffer) at 37° C., 5% CO2. Cells were then aliquoted (200,000 cells/well) into a sterile, clear, tissue cultured coated 24-well plate. To evaluate agglutination, cells were incubated with G1, G1-PEG-G1, G1/G3 or G1/G3 Dimer (final [G3]=5 μM or 0.5 μM) and then imaged at 4 hours using a Zeiss Axio Observer inverted microscope. Following imaging, cells were harvested from the wells and washed with 10 mL of cold 100 mM (3-lactose to remove bound galectins followed by centrifugation at 413×g for 7 min on a Centrifuge 5804R (Eppendorf). Supernatant was removed thereafter and cells were resuspended in 200 μL 1× Annexin V binding buffer. 100 μL of each sample (100,000 cells) was transferred into a 96 well plate, and then 1 μL of FITC-Annexin V and 1 μL of PI (BD556547, ThermoFisher) were added to each well. Samples were incubated for 15 minutes protected from light, and then both brightfield and fluorescence images were collected. Images were taken on a Zeiss Axio Observer inverted microscope with FITC (excitation=470/40 nm and emission=525/50 nm) and rhodamine (excitation=546/12 nm and emission=575-640 nm) filter sets.

Jurkat T Cell Metabolic Activity

Jurkat T cells were aliquoted into sterile, clear, non-tissue culture coated 96-well microplates (20,000 cells/well). In some experiments, cells were cultured in complete media, while in others cells were cultured in complete serum-free media. Cells were incubated with G1, G1-PEG-G1, G1/G3 or G1/G3 Dimer (final [G3]=5 μM or 0.5 μM) for 18 hours and then imaged using a Zeiss Axio Observer inverted microscope. Following imaging, cells were treated with 20 μL of CellTiter-Blue® reagent (PR-G8080, Promega) for 2 hours. Fluorescence emission of each well was measured using a SpectraMax M3 plate reader (excitation=560 nm, emission=590 nm).

Micron-Sized Particulate Analysis

Micron-sized particulates were observed when G1/G3 Dimer was mixed with serum containing media. To characterize the involvement of serum glycoproteins, 50 μL of complete Media or complete serum-free media (RPMI 1640 supplemented with 1% penicillin—streptomycin, L-glutamine 200 mM, 1% HEPES buffer) was mixed with 50 μL of a PBS solution containing 10 μM of G1/G3 dimer. Immediately after pipetting the media and protein samples, kinetic turbidity measurements were collected as described above. Brightfield images of samples allowed to settle for 15 minutes were then collected using a Zeiss Axio Observer inverted microscope.

To determine if turbidity changes were due to specific glycoprotein-galectin interactions, 50 μL PBS with or without 10 μM G1/G3 dimer was mixed 50 μL of either serum-free complete media or complete media and incubated for 10 minutes. Then, samples were treated with an additional 50 µL of PBS or PBS containing 100 mM β-Lactose before sample turbidity was measured via absorbance at 420 nm.

To determine the dependence of aggregation on serum glycoprotein concentration, complete media was diluted with complete serum-free media to 1%, 0.5%, and 0.1% serum. 50 µL of each media type mixed with 50 µL of PBS containing 10 µM of G1/G3 protein was allowed to incubate for 10 minutes, after which absorbance at 420 nm was measured.

Statistical Analysis

All experimental and control groups had at least n=4 for binding affinity, Jurkat T cell apoptosis studies, and Jurkat T cell metabolic activity studies. A representative graph was shown for binding affinity studies. Data was analyzed for statistically significant differences using one-way ANOVA with Tukey's post hoc (p=0.05) or two-tailed t test (p=0.05) in GraphPad Prism software. Protein sequences were SEQ ID NOS: 1-3.

Example 2: G1/G3 Zipper can Halt Inflammation

Figure 13:
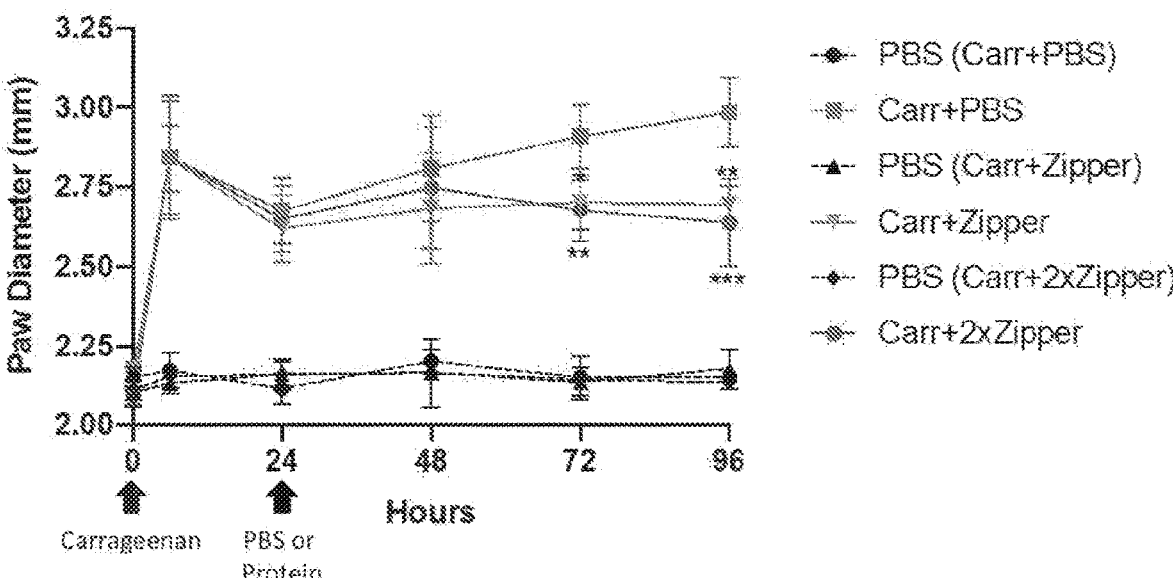
FIG. 13 shows that local injection of G1/G3 fusion protein ("Zipper") halts the inflammation induced by carrageenan. Mice were administered lambda-carrageenan or PBS as control. Administrations of control were performed on contralateral feet of the mice. Experimental groups: PBS+1% Carr (experimental control); 1% Carr+0.3 microg/microL (μg/μL) Zipper; 1% Carr+0.6 microg/microL ("2×") Zipper. "PBS (Carr+PBS)", "PBS (Carr+Zipper)", and "PBS (Carr+2× Zipper)" denote measurements made on the contralateral foot that received PBS only as the vehicle control.

Mice were administered lambda-carrageenan or PBS as control. Administrations of control were performed on contralateral feet of the mice. Experimental groups: PBS+1% Carr (experimental control); 1% Carr+0.3 microg/microL (µg/µL) Zipper; 1% Carr+0.6 microg/microL ("2×") Zipper. "PBS (Carr+PBS)", "PBS (Carr+Zipper)", and "PBS (Carr+ 2× Zipper)" denote measurements made on the contralateral foot that received PBS only as the vehicle control. As can be seen in FIG. 13, local injection of G1/G3 fusion protein ("Zipper") halts the inflammation induced by carrageenan.

REFERENCES

1. A. Alavi and J. Axford, *Rheumatology*, 2008, 47, 760-770.
2. H. Schachter, *Journal of Clinical Investigation*, 2001, 108, 1579-1582.
3. H. Leffler, S. Carlsson, M. Hedlund, Y. Qian and F. Poirier, *Glycoconjugate Journal*, 2002, 19, 433-440.
4. S. Farhadi and G. Hudalla, *Experimental Biology and Medicine*, 2016, 241, 1074-1083.
5. G. Rabinovich, G. Daly, H. Dreja, H. Tailor, C. Riera, J. Hirabayashi and A. Chernajovsky, *Journal of Experimental Medicine*, 1999, 190, 385-397.
6. L. Santucci, S. Fiorucci, N. Rubinstein, A. Mencarelli, B. Palazzetti, B. Federici, G. Rabinovich and A. Morelli, *Gastroenterology*, 2003, 124, 1381-1394.
7. S. Starossom, I. Mascanfroni, J. Imitola, L. Cao, K. Raddassi, S. Hernandez, R. Bassil, D. Croci, J. Cerliani, D. Delacour, Y. Wang, W. Elyaman, S. Khoury and G. Rabinovich, *Immunity*, 2012, 37, 249-263.
8. M. Toscano, A. Commodaro, J. Ilarregui, G. Bianco, A. Liberman, H. Serra, J. Hirabayashi, L. Rizzo and G. Rabinovich, *Journal of Immunology*, 2006, 176, 6323-6332.
9. S. Blois, J. Ilarregui, M. Tometten, M. Garcia, A. Orsal, R. Cordo-Russo, M. Toscano, G. Bianco, P. Kobelt, B. Handjiski, I. Tirado, U. Markert, B. Klapp, F. Poirier, J. Szekeres-Bartho, G. Rabinovich and P. Arck, *Nature Medicine*, 2007, 13, 1450-1457.
10. C. St-Pierre, H. Manya, M. Ouellet, G. Clark, T. Endo, M. Tremblay and S. Sato, *Journal of Virology*, 2011, 85, 11742-11751.
11. P. Barrionuevo, M. Beigier-Bompadre, J. Ilarregui, M. Toscano, G. Bianco, M. Isturiz and G. Rabinovich, *Journal of Immunology*, 2007, 178, 436-445.
12. S. Correa, C. Sotomayor, M. Aoki, C. Maldonado and G. Rabinovich, *Glycobiology*, 2003, 13, 119-128.
13. G. Rabinovich, C. Sotomayor, C. Riera, I. Bianco and S. Correa, *European Journal of Immunology*, 2000, 30, 1331-1339.
14. J. M. Ilarregui, D. O. Croci, G. A. Bianco, M. A. Toscano, M. Salatino, M. E. Vermeulen, J. R. Geffner and G. A. Rabinovich, *Nature Immunology*, 2009, 10, 981-U975.
15. C. Auvynet, S. Moreno, E. Melchy, I. Coronado-Martinez, J. Montiel, I. Aguilar-Delfin and Y. Rosenstein, *Glycobiology*, 2013, 23, 32-42.
16. A. MacKinnon, S. Farnworth, P. Hodkinson, N. Henderson, K. Atkinson, H. Leffler, U. Nilsson, C. Haslett, S. Forbes and T. Sethi, *Journal of Immunology*, 2008, 180, 2650-2658.
17. A. Dragomir, R. Sun, H. Choi, J. Laskin and D. Laskin, *Journal of Immunology*, 2012, 189, 5934-5941.
18. I. Kuwabara and F. Liu, *Journal of Immunology*, 1996, 156, 3939-3944.
19. H. Chen, I. Weng, E. Maverakis, R. Yang, D. Hsu and F. Liu, *Journal of Immunology*, 2007, 178.
20. A. Grigorian, S. Torossian and M. Demetriou, *Immunological Reviews*, 2009, 230, 232-246.
21. H. Walzel, U. Schulz, P. Neels and J. Brock, *Immunology Letters*, 1999, 67, 193-202.
22. B. Stillman, D. Hsu, M. Pang, C. Brewer, P. Johnson, F. Liu and L. Baum, *Journal of Immunology*, 2006, 176, 778-789.
23. K. Pace, C. Lee, P. Stewart and L. Baum, *Journal of Immunology*, 1999, 163, 3801-3811.
24. M. Elola, M. Chiesa, A. Alberti, J. Mordoh and N. Fink, Journal of Biomedical *Science*, 2005, 12, 13-29.
25. M. Toscano, G. Bianco, J. Ilarregui, D. Croci, J. Correale, J. Hernandez, N. Zwirner, F. Poirier, E. Riley, L. Baum and G. Rabinovich, *Nature Immunology*, 2007, 8, 825-834.
26. M. Tribulatti, M. Figini, J. Carabelli, V. Cattaneo and O. Campetella, *Journal of Immunology*, 2012, 188, 2991-2999.
27. D. Hsu, S. Hammes, I. Kuwabara, W. Greene and F. Liu, *American Journal of Pathology*, 1996, 148, 1661-1670.
28. F. Cedeno-Laurent, M. Opperman, S. Barthel, V. Kuchroo and C. Dimitroff, *Journal of Immunology*, 2012, 188, 3127-3137.
29. L. Santucci, S. Fiorucci, F. Cammilleri, G. Servillo, B. Federici and A. Morelli, *Hepatology*, 2000, 31, 399-406.
30. L. Baum, D. Blackall, S. Arias-Magallano, D. Nanigian, S. Uh, J. Browne, D. Hoffmann, C. Emmanouilides, M. Territo and G. Baldwin, *Clinical Immunology*, 2003, 109, 295-307.
31. G. Levi, R. Tarrabhazdai and V. Teichberg, *European Journal of Immunology*, 1983, 13, 500-507.
32. H. Offner, B. Celnik, T. Bringman, D. Casentiniborocz, G. Nedwin and A. Vandenbark, *Journal of Neuroimmunology*, 1990, 28, 177-184.
33. V. Giudicelli, D. Lutomski, M. LeviStrauss, D. Bladier, R. JoubertCaron and M. Caron, *Glycobiology*, 1997, 7, R8-R10.
34. F. Cedeno-Laurent, S. Barthel, M. Opperman, D. Lee, R. Clark and C. Dimitroff, *Journal of Immunology*, 2010, 185, 4659-4672.
35. L. Earl, S. Bi and L. Baum, *Glycobiology*, 2011, 21, 6-12.
36. J. van der Leij, A. van den Berg, G. Harms, H. Eschbach, H. Vos, P. Zwiers, R. van Weeghel, H. Groen, S. Poppema and L. Visser, *Molecular Immunology*, 2007, 44, 506-513.

US 12,577,282 B2

47

48

37. M. Fettis and G. Hudalla, *Bioconjugate Chemistry*, 2018, 29, 2489-2496.
38. J. Kopitz, S. Vertesy, S. Andre, S. Fiedler, M. Schnolzer and H. Gabius, Biochimie, 2014, 104, 90-99.
39. M. Berbis, S. Andre, F. Canada, R. Pipkorn, H. Ippel, K. Mayo, D. Kubler, H. Gabius and J. Jimenez-Barbero, *Biochemical and Biophysical Research Communications*, 2014, 443, 126-131.
40. S. Farhadi, E. Bracho-Sanchez, M. Fettis, D. Seroski, S. Freeman, A. Restuccia, B. Keselowsky and G. Hudalla, *Nature Communications*, 2018, 9.
41. B. Collins and J. Paulson, *Current Opinion in Chemical Biology*, 2004, 8, 617-625.
42. P. Mittl, C. Deillon, D. Sargent, N. Liu, S. Klauser, R. Thomas, B. Gutte and M. Grutter, *Proceedings of the National Academy of Sciences of the United States of America*, 2000, 97, 2562-2566.
43. C. Guardia, J. Caramelo, M. Trujillo, S. Mendez-Huergo, R. Radi, D. Estrin and G. Rabinovich, *Glycobiology*, 2014, 24, 428-441.
44. M. Fettis and G. Hudalla, *Bioconjugate Chemistry*, 2018, 29, 2489-2496.
45. N. Nishi, A. Abe, J. Iwaki, H. Yoshida, A. Itoh, H. Shoji, S. Kamitori, J. Hirabayashi and T. Nakamura, *Glycobiology*, 2008, 18, 1065-1073.
46. T. Dam, H. Gabius, S. Andre, H. Kaltner, M. Lensch and C. Brewer, *Glycobiology*, 2005, 15, 1215-1215.
47. C. Goodman, M. Wolfenden, P. Nangia-Makker, A. Michel, A. Raz and M. Cloninger, Beilstein *Journal of Organic Chemistry*, 2014, 10, 1570-1577.
48. J. Sacchettini, L. Baum and C. Brewer, *Biochemistry*, 2001, 40, 3009-3015.
49. O. Garner and L. Baum, *Biochemical Society Transactions*, 2008, 36, 1472-1477.
50. G. Rabinovich, M. Toscanol, S. Jackson and G. Vasta, *Current Opinion in Structural Biology*, 2007, 17, 513-520.
51. I. Nabi, J. Shankar and J. Dennis, *Journal of Cell Science*, 2015, 128, 2213-2219.
52. B. Belardi, G. O'Donoghue, A. Smith, J. Groves and C. Bertozzi, *Journal of the American Chemical Society*, 2012, 134, 9549-9552.
53. D. Mandal and C. Brewer, *Biochemistry*, 1992, 31, 8465-8472.
54. N. Perillo, K. Pace, J. Seilhamer and L. Baum, *Nature*, 1995, 378, 736-739.
55. N. Perillo, C. Uittenbogaart, J. Nguyen and L. Baum, *Journal of Experimental Medicine*, 1997, 185, 1851-1858.
56. C. Cederfur, E. Salomonsson, J. Nilsson, A. Halim, C. Oeberg, G. Larson, U. Nilsson and H. Leffler, *Glycobiology*, 2008, 18, 384-394.
57. A. Restuccia, M. Fettis, S. Farhadi, M. Molinaro, B. Kane and G. Hudalla, *ACS Biomaterials Science & Engineering*, 2018, 4, 3451-3459.
58. L. Candeias, D. MacFarlane, S. McWhinnie, N. Maidwell, C. Roeschlaub, P. Sammes and R. Whittlesey, *Journal of the Chemical Society-Perkin Transactions*, 1998, 2, 2333-2334.

EXEMPLARY SEQUENCES

This Table exhibits some exemplary sequences as disclosed by the instant Specification, but is not limiting. This Specification includes a Sequence Listing submitted concurrently herewith as a text file in ASCII format. The Sequence Listing and all of the information contained therein are expressly incorporated herein and constitute part of the instant Specification as filed.

TABLE 1

Exemplary Sequences

| SEQ ID NO: | Sequence* | Description** |
|---|---|---|
| 1 | MASGLVASNLNLKPGESLRVRGEVAPDAKS FVLNLGKDSNNLCLHFNPRFNAHGDANTIV CNSKDGGAWGTEQREAVFPFQPGSVAEVSI TFDQANLTVKLPDGYEFKFPNRLNLEAINY MAVDGDFKIKSVAFD | G1 Protein Sequence (AA) |
| 2 | MASGLVASNLNLKPGESLRVRGEVAPDAKS FVLNLGKDSNNLCLHFNPRFNAHGDANTIV CNSKDGGAWGTEQREAVFPFQPGSVAEVSI TFDQANLTVKLPDGYEFKFPNRLNLEAINY MAADGDFKIKSVAFDGSGGGSGGSGGSGGE FADNFSLHDALSGSGNPNPQGWPGAWGNQ PAGAGGYPGASYPGAYPGQAPPGAYPGQAP PGAYPGAPGAYPGAPAPGVYPGPPSGPGAY PSSGQPSAPGAYPATGPYGAPAGPLIVPYNL PLPGGVVPRMLITILGTVKPNANRIALDFQR GNDVAFHFNPRFNENNRRVIVCNTKLDNNW GREERQSVFPFESGKPFKIQVLVEPDHFKVA VNDAHLLQYNHRVKKLNEISKLGISGDIDLT SASYNMILEHHHHHH | G1/G3 Protein Sequence with optional C-terminal His tag (bold & underlined) (AA) |
| 3 | MASGLVASNLNLKPGESLRVRGEVAPDAKS FVLNLGKDSNNLCLHFNPRFNAHGDANTIV CNSKDGGAWGTEQREAVFPFQPGSVAEVSI TFDQANLTVKLPDGYEFKFPNRLNLEAINY MAADGDFKIKSVAFDGSGGGSGGSGGSGG MARMKQLEDKVEELLSKNYHLENEVARLK KLVGERGGGSGGSGGGGSGGSGGEFADNFS LHDALSGSGNPNPQGWPGAWGNQPAGAGG YPGASYPGAYPGQAPPGAYPGQAPPGAYPG | G1/G3 Protein Dimer sequence with optional C-terminal His tag (bold & underlined) (AA) |

TABLE 1-continued

| | Exemplary Sequences | |
|---|---|---|

| SEQ ID NO: | Sequence* | Description** |
|---|---|---|
| | APGAYPGAPAPGVYPGPPSGPGAYPSSGQPS APGAYPATGPYGAPAGPLIVPYNLPLPGGV VPRMLITILGTVKPNANRIALDFQRGNDVAF HFNPRFNENNRRVIVCNTKLDNNWGREERQ SVFPPFESGKPFKIQVLVEPDHFKVAVNDAHL LQYNHRVKKLNEISKLGISGDIDLTSASYNM ILE<u>HHHHHH</u> | |
| 4 | EFADNFSLHDALSGSGNPNPQGWPGAWGN QPAGAGGYPGASYPGAYPGQAPPGAYPGQ APPGAYPGAPGAYPGAPAPGVYPGPPSGPG AYPSSGQPSAPGAYPATGPYGAPAGPLIVPY NLPLPGGVVPRMLITILGTVKPNANRIALDF QRGNDVAFHFNPRFNENNRRVIVCNTKLDN NWGREERQSVFPPFESGKPFKIQVLVEPDHFK VAVNDAHLLQYNHRVKKLNEISKLGISGDI DLTSASYNMILE<u>HHHHHH</u> | Galectin-3 with the C-terminal His Tag (bold & underlined) (AA) |
| 5 | GSGGGSGGSGGSGG<u>MARMKQLEDKVEEL LSKNYHLENEVARLKKLVGER</u>GGGSGGSG GGGSGGSGG | Coiled-Coiled linker region (Dimer) (dimerization sequence is bold & underlined) (AA) |
| 6 | ATGGCTAGTGGTCTGGTCGCCAGCAACCT GAATCTCAAACCTGGAGAGAGCCTTCGAG TGCGAGGCGAGGTGGCTCCTGACGCTAAG AGCTTCGTGCTGAACCTGGGCAAAGACAG CAACAACCTGTGCCTGCACTTCAACCCTCG CTTCAACGCCCACGGCGACGCCAACACCA TCGTGTGCAACAGCAAGGACGGCGGGGCC TGGGGGACCGAGCAGCGGGAGGCTGTCTT TCCCTTCCAGCCTGGAAGTGTTGCAGAGG TGAGCATCACCTTCGACCAGGCCAACCTG ACCGTCAAGCTGCCAGATGGATACGAGTT CAAGTTCCCCAACCGCCTCAACCTGGAGG CCATCAACTACATGGCAGCTGACGGTGAC TTCAAGATCAAAAGTGTGGCCTTTGACGG ATCCGGCGGCGGCAGCGGCGGCAGCGGCG GCAGCGGCGGCATGGCGCGCATGAAACAG CTGGAAGATAAAGTGGAAGAACTGCTGAG CAAAAACTATCATCTGGAAAACGAAGTGG CGCGCCTGAAAAAACTGGTGGGCGAACGC GGCGGCGGCAGCGGCGGCAGCGGCGGCG GCGGCAGCGGCGGCAGCGGCGAATTCGCA GACAATTTTTCGCTCCATGATGCGTTATCT GGGTCTGGAAACCCAAACCCTCAAGGATG GCCTGGCGCATGGGGGAACCAGCCTGCTG GGGCAGGGGGCTACCCAGGGGCTTCCTAT CCTGGGGCCTACCCCGGGCAGGCACCCCC AGGGGCTTATCCTGGACAGGCACCTCCAG GCGCCTACCCTGGAGCACCTGGAGCTTAT CCCGGAGCACCTGCACCTGGAGTCTACCC AGGGCCACCCAGCGGCCCTGGGGCCTACC CATCTTCTGGACAGCCAAGTGCCCCCGGA GCCTACCCTGCCACTGGCCCCTATGGCGCC CCTGCTGGGCCACTGATTGTGCCTTATAAC CTGCCTTTGCCTGGGGGAGTGGTGCCTCGC ATGCTGATAACAATTCTGGGCACGGTGAA GCCCAATGCAAACAGAATTGCTTTAGATT TCCAAAGAGGGAATGATGTTGCCTTCCAC TTTAACCCACGCTTCAATGAGAACAACAG GAGAGTCATTGTTTGCAATACAAAGCTGG ATAATAACTGGGGAAGGGAAGAAAGACA GTCGGTTTTCCCATTTGAAAGTGGGAAAC CATTCAAAATACAAGTACTGGTTGAACCT GACCACTTCAAGGTTGCAGTGAATGATGC TCACTTGTTGCAGTACAATCATCGGGTTAA AAAACTCAATGAAATCAGCAAACTGGGAA TTTCTGGTGACATAGACCTCACCAGTGCTT CATATAACATGATACTCGAG | G1/G3 Dimer nucleotide sequence (NT) |
| 7 | ATG GCT AGT GGT CTG GTC GCC AGC AAC CTG AAT CTC AAA CCT GGA GAG AGC CTT | G1 nucleotide sequence (NT) |

TABLE 1-continued

Exemplary Sequences

| SEQ ID NO: | Sequence* | Description** |
|---|---|---|
| | CGA GTG CGA GGC GAG GTG GCT CCT<br>GAC GCT AAG AGC TTC GTG CTG AAC CTG<br>GGC AAA GAC AGC AAC AAC CTG TGC<br>CTG CAC TTC AAC CCT CGC TTC AAC GCC<br>CAC GGC GAC GCC AAC ACC ATC GTG<br>TGC AAC AGC AAG GAC GGC GGG GCC<br>TGG GGG ACC GAG CAG CGG GAG GCT<br>GTC TTT CCC TTC CAG CCT GGA AGT GTT<br>GCA GAG GTG AGC ATC ACC TTC GAC<br>CAG GCC AAC CTG ACC GTC AAG CTG<br>CCA GAT GGA TAC GAG TTC AAG TTC CCC<br>AAC CGC CTC AAC CTG GAG GCC ATC<br>AAC TAC ATG GCA GCT GAC GGT GAC TTC<br>AAG ATC AAA AGT GTG GCC TTT GAC | |
| 8 | GCAGACAATTTTTCGCTCCATGATGCGTTA<br>TCTGGGTCTGGAAACCCAAACCCTCAAGG<br>ATGGCCTGGCGCATGGGGGAACCAGCCTG<br>CTGGGGCAGGGGGCTACCCAGGGGCTTCC<br>TATCCTGGGGCCTACCCCGGGCAGGCACC<br>CCCAGGGGCTTATCCTGGACAGGCACCTC<br>CAGGCGCCTACCCTGGAGCACCTGGAGCT<br>TATCCCGGAGCACCTGCACCTGGAGTCTA<br>CCCAGGGCCACCCAGCGGCCCTGGGGCCT<br>ACCCATCTTCTGGACAGCCAAGTGCCCCC<br>GGAGCCTACCCTGCCACTGGCCCCTATGG<br>CGCCCCTGCTGGGCCACTGATTGTGCCTTA<br>TAACCTGCCTTTGCCTGGGGGAGTGGTGC<br>CTCGCATGCTGATAACAATTCTGGGCACG<br>GTGAAGCCCAATGCAAACAGAATTGCTTT<br>AGATTTCCAAAGAGGGAATGATGTTGCCT<br>TCCACTTTAACCCACGCTTCAATGAGAAC<br>AACAGGAGAGTCATTGTTTGCAATACAAA<br>GCTGGATAATAACTGGGGAAGGGAAGAAA<br>GACAGTCGGTTTTCCCATTTGAAAGTGGG<br>AAACCATTCAAAATACAAGTACTGGTTGA<br>ACCTGACCACTTCAAGGTTGCAGTGAATG<br>ATGCTCACTTGTTGCAGTACAATCATCGGG<br>TTAAAAAACTCAATGAAATCAGCAAACTG<br>GGAATTTCTGGTGACATAGACCTCACCAG<br>TGCTTCATATAACATGATA | G3 nucleotide sequence (NT) |
| 9 | MARMKQLEDKVEELLSKNYHLENEVARLK<br>KLVGER | Dimerization Sequence (AA) |
| 10 | GSGGGSGGSGGSGG | Linker Sequence (AA) |
| 11 | GGGSGGSGGGGSGGSGG | Linker Sequence (AA) |

*Unless otherwise specified, nucleic acid sequences are described 5' to 3' and amino acid sequences are described N-terminus to C-terminus
**'NT' denotes a nucleic acid sequence; 'AA' denotes an amino acid sequence.

---

What is claimed is:

1. A Galectin-1/Galectin-3 (Gal-1/Gal-3) dimer comprising:

two monomer polypeptides, wherein each monomer polypeptide comprises:

a Galectin-1 (Gal-1) polypeptide;

a Galectin-3 (Gal-3) polypeptide; and a linker comprising an alpha helix coil, wherein the alpha helix coil comprises the sequence of SEQ ID NO: 9, wherein the linker is fused between the Gal-1 polypeptide and the Gal-3 polypeptide, wherein the two monomer polypeptides associate with each other via dimerization at the alpha helix coils to form the Gal-1/Gal-3 dimer, wherein one or both of the monomer polypeptides has a sequence that is about 90% to about 100% identical to SEQ ID NO: 3.

2. The Gal-1/Gal-3 dimer of claim 1, wherein the Gal-1 polypeptide has a sequence that is about 80% to about 100% identical to SEQ ID NO: 1.

3. The Gal-1/Gal-3 dimer of claim 1, wherein the Gal-3 polypeptide has a sequence that is about 80% to about 100% identical to SEQ ID NO: 4.

4. The Gal-1/Gal-3 dimer of claim 1, wherein the alpha helix coil has a sequence that is about 80% to about 100% identical to SEQ ID NO: 5.

5. A pharmaceutical formulation comprising:

the Galectin-1/Galectin-3 (Gal-1/Gal-3) dimer of claim 1; and a pharmaceutically acceptable carrier.

6. A Galectin-1/Galectin-3 (Gal-1/Gal-3) polypeptide capable of dimerizing comprising:

a Galectin-1 (Gal-1) polypeptide;

a Galectin-3 (Gal-3) polypeptide; and a linker comprising an alpha helix coil, wherein the alpha helix coil comprises the sequence of SEQ ID NO: 9, wherein the linker is fused between the Gal-1 polypeptide and the Gal-3 polypeptide, wherein the Gal-1/ Gal-3 polypeptide has a sequence that is about 90% to about 100% identical to SEQ ID NO: 3.

7. The Galectin-1/Galectin-3 (Gal-1/Gal-3) dimer of claim 1, wherein:

(i) the Gal-1 polypeptide in at least one of the monomer polypeptides comprises the sequence of SEQ ID NO: 1;

(ii) the linker in at least one of the monomer polypeptides comprises the sequence of any one of SEQ ID NOs: 5, 10, or 11;

and/or (iii) at least one of the monomer polypeptides does not comprise an N-terminal tag or a C-terminal tag.

8. A pharmaceutical formulation comprising:

a plurality of the Galectin-1/Galectin-3 (Gal-1/Gal-3) polypeptide of claim 6; and a pharmaceutically acceptable carrier.

9. The Gal-1/Gal-3 polypeptide of claim 6, wherein the Gal-1 polypeptide has a sequence that is about 80% to about 100% identical to SEQ ID NO: 1.

10. The Gal-1/Gal-3 polypeptide of claim 6, wherein the Gal-3 polypeptide has a sequence that is about 80% to about 100% identical to SEQ ID NO: 4.

11. The Gal-1/Gal-3 polypeptide of claim 6, wherein the alpha helix coil has a sequence that is about 80% to about 100% identical to SEQ ID NO: 5.

12. The Galectin-1/Galectin-3 (Gal-1/Gal-3) polypeptide of claim 6, wherein:

(i) the Gal-1 polypeptide comprises the sequence of SEQ ID NO: 1;

(ii) the linker comprises the sequence of any one of SEQ ID NOs: 5, 10, or 11;

and/or (iii) the Gal-1/Gal-3 polypeptide does not comprise an N-terminal tag or a C-terminal tag.

13. A Galectin-1/Galectin-3 (Gal-1/Gal-3) polynucleotide comprising:

a polynucleotide that encodes a Galectin-1 (Gal-1) polypeptide;

a polynucleotide that encodes a Galectin-3 (Gal-3) polypeptide; and a polynucleotide that encodes a linker comprising an alpha helix coil, wherein the alpha helix coil comprises the sequence of SEQ ID NO: 9, wherein the polynucleotide that encodes the alpha helix coil is fused in-frame between the polynucleotide that encodes the Gal-1 polypeptide and the polynucleotide that encodes the Gal-3 polypeptide, wherein the Gal-1/Gal-3 polynucleotide encodes a polypeptide having a sequence that is about 90% to about 100% identical to SEQ ID NO: 3.

14. The Gal-1/Gal-3 polynucleotide of claim 13, wherein the Gal-1 polypeptide has a sequence that is about 80% to about 100% identical to SEQ ID NO: 1.

15. The Gal-1/Gal-3 polynucleotide of claim 13, wherein the Gal-3 polypeptide has a sequence that is about 80% to about 100% identical to SEQ ID NO: 4.

16. The Gal-1/Gal-3 polynucleotide of claim 13, wherein the alpha helix coil has a sequence that is about 80% to about 100% identical to SEQ ID NO: 5.

17. A vector comprising:

the Gal-1/Gal-3 polynucleotide of claim 13.

18. A bacterial cell comprising:

the polynucleotide sequence of claim 13.

19. A method for reducing inflammation comprising: administering the Galectin-1/Galectin-3 (Gal-1/Gal-3) dimer of claim 1 or a pharmaceutical formulation comprising the Galectin-1/Galectin-3 (Gal-1/Gal-3) dimer of claim 1 to a subject in need thereof.

* * * * *